(12) United States Patent
Mukai et al.

(10) Patent No.: US 7,588,705 B2
(45) Date of Patent: Sep. 15, 2009

(54) SKIN NEEDLE MANUFACTURING APPARATUS AND SKIN NEEDLE MANUFACTURING METHOD

(75) Inventors: Nobuyuki Mukai, Tokyo (JP); Shuken Kuramoto, Tokyo (JP); Tsutomu Takahashi, Tokyo (JP); Yoshinori Oonuma, Tokyo (JP)

(73) Assignee: Nabtesco Corporation, Tokyo (JP)

( * ) Notice: Subject to any disclaimer, the term of this patent is extended or adjusted under 35 U.S.C. 154(b) by 260 days.

(21) Appl. No.: 11/794,364

(22) PCT Filed: Dec. 28, 2005

(86) PCT No.: PCT/JP2005/024136

§ 371 (c)(1),
(2), (4) Date: Jun. 28, 2007

(87) PCT Pub. No.: WO2006/077742

PCT Pub. Date: Jul. 27, 2006

(65) Prior Publication Data

US 2008/0157421 A1    Jul. 3, 2008

(30) Foreign Application Priority Data

Dec. 28, 2004    (JP) .............................. 2004-380881

(51) Int. Cl.
*B29C 51/00*    (2006.01)

(52) U.S. Cl. ........................ 264/164; 264/243; 425/135; 425/144; 425/149; 425/167

(58) Field of Classification Search .................. None
See application file for complete search history.

(56) References Cited

FOREIGN PATENT DOCUMENTS

| JP | 2-39467 Y2 | 10/1990 |
|----|------------|---------|
| JP | 3-32377 B2 | 5/1991 |
| JP | 2002-517300 A | 6/2002 |
| JP | 2003-238347 A | 8/2003 |
| WO | 99/64580 A1 | 12/1999 |
| WO | 02/100474 A2 | 12/2002 |
| WO | 03/020359 A2 | 3/2003 |
| WO | 2004/108204 A1 | 12/2004 |

*Primary Examiner*—Monica A Huson
(74) *Attorney, Agent, or Firm*—Panitch Schwarze Belisario & Nadel LLP

(57) ABSTRACT

In a skin needle manufacturing apparatus 10, a material melted in a syringe 45 is discharged from a fine hole 47a of a pin member 47 and is caused to adhere to a base 48. A computer 50 causes a drive mechanism 48 to separate the pin member 47 from the base 48. Then, the material 80 having adhered to the pin member 47 and the base 48 is drawn out. A projection portion 48b formed of a part of the material 80, which has adhered to the base 48, is formed into a skin needle 81. Consequently, a skin needle can relatively easily be manufactured without requiring excessive time, effort, and cost.

42 Claims, 16 Drawing Sheets

FIG. 27
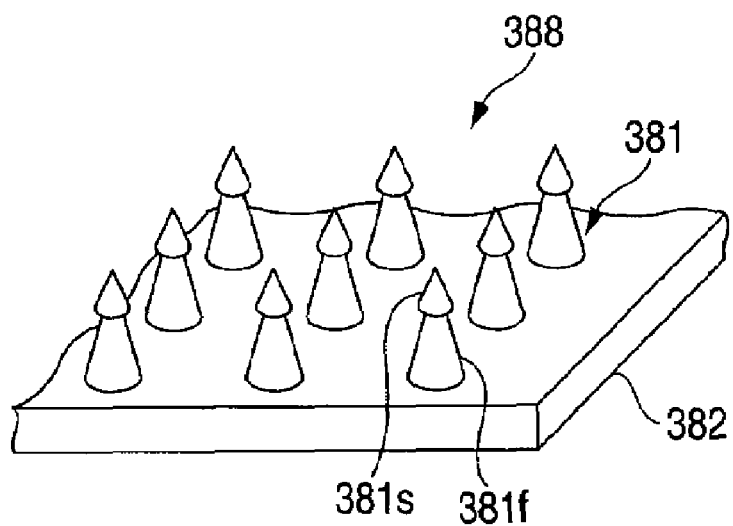
FIG. 28 (a)
FIG. 28 (b)
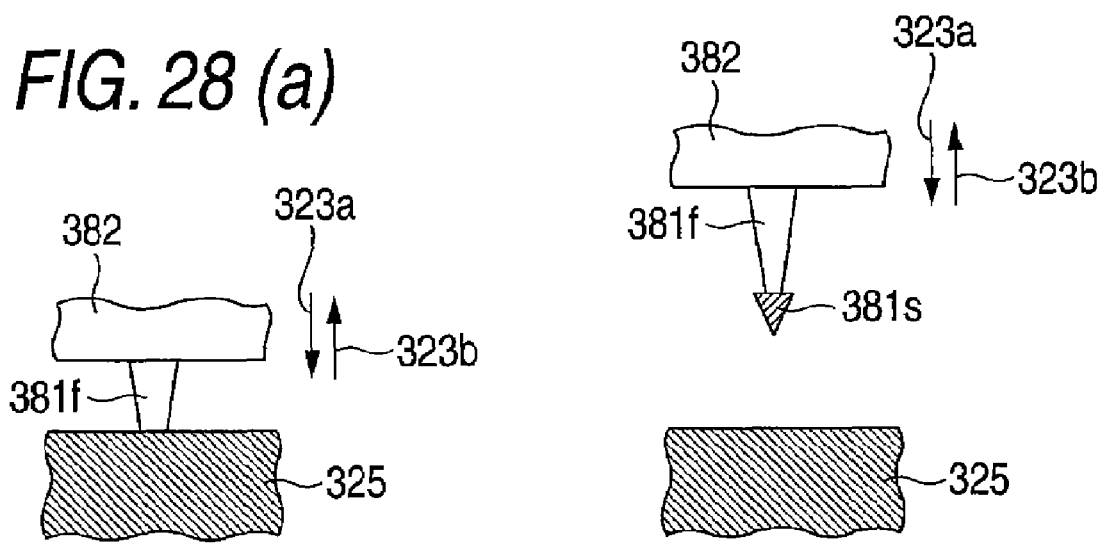

SKIN NEEDLE MANUFACTURING APPARATUS AND SKIN NEEDLE MANUFACTURING METHOD

CROSS-REFERENCE TO RELATED APPLICATIONS

This application is a Section 371 of International Application No. PCT/JP2005/024136, filed Dec. 28, 2005, which was published in the Japanese language on Jul. 27, 2006, under International Publication No. WO 2006/077742 A1 and the disclosure of which is incorporated herein by reference.

BACKGROUND OF THE INVENTION

The present invention relates to a manufacturing apparatus and method for manufacturing needles that are stabbed into skin and that are used for medical treatment and beautification.

Skin needles can stab into human skin by being arranged to erect on, for example, the top surface of a sheet-like base, whose length ranges from 50 μm to 1 mm, and being held thereto. In a case where the needles are finely formed, a stabbed person feels no pain. In a case where the skin needle is formed of a material which employs biodegradable substances (e.g., maltose (or malt sugar) and polylactic acid) as major ingredients and is mixed with functional substances including cosmetic ingredients and effective ingredients, a tip part of the needle melts after inserted into the skin. Thus, the ingredients of the material can be injected into the skin. A person stabbed by the skin needle can obtain various effects according to the ingredients. For example, in a case where the material of a needle includes colorants, such as food red, as a gradient thereof, the person stabbed by the needle can obtain cosmetic effects on his skin. In a case where the material of a needle includes an ultraviolet absorber, skin stabbed by the needle can obtain a sunburn prevention effect. Additionally, in a case where the material of a needle is mixed with a medical agent, such as insulin, diabetes can be treated and prevented by stabbing skin with the needle.

Hitherto, a method of forming such a skin needle by injecting a material into a mold has been known as a conventional manufacturing method for such a skin needle (see, e.g., Patent Document 1). Patent Document 1: JP-A-2003-238347 (page 4)

The degree of effects obtained at the time of stabbing skin with skin needles can be adjusted according to the sizes and the number of the skin needles. Also, the length, the thickness, and the shape of such a skin needle are appropriately adjusted according to the material and the purpose thereof. According to the conventional manufacturing method, in a case where appropriate needles are manufactured, it is necessary to prepare several molds respectively corresponding to the needles. In a case where the number of the molds is large, the time and effort for preparing the molds and those for managing the molds are very large. Additionally, the mold for forming micro-needles needs precisely shaping and is apt to be costly. Thus, the conventional manufacturing method has a problem that the time, the effort and the cost are excessive. Such a problem is inevitable, especially, in cases where it is intended to manufacture various kinds of skin needles little by little and where it is intended to tentatively manufacture a small number of skin needles.

BRIEF SUMMARY OF THE INVENTION

An object of the invention is to provide a skin-needle manufacturing apparatus and method enabled to relatively easily manufacture skin needles without excessive time, effort, and cost.

The invention features that a skin needle is formed by drawing out molten material. The material of the needle in a molten state is attached to one and the other of members. Then, both the members are drawn away from each other (i.e., both the members are moved in a direction in which the members relatively move away from each other), so that the material positioned between both the members is drawn out by being pulled by both the members. At that time, the drawn-out material is gradually tapered toward opposite to each of adhesion portions respectively attached to the members (i.e., needle-shaped). Fundamentally, the invention uses the needle-shaped portions as skin needles.

According to the invention, the material of the needle in a molten state is provided on the base on which the needle is erected. The pin member is attached to a part of the molten material. That is, the material of the needle in a molten state is attached to the base and the pin member. The molten material can be drawn out by relatively pulling the base and the pin member in a direction in which the base and the pin member move away from each other. The drawn-out material includes a portion (i.e., an adhesion portion) adhering to one of the members, i.e., the pin member, and also includes the other member (i.e., the projection portion). The projection portion adhering to the base is protruded by a tensile force generated between the base and the adhesion portion provided at the side of the pin member so that the projection portion is tapered toward an end thereof (i.e., toward opposite to the base). When the adhesion portion is cut off from the projection portion, the projection portion erected on the base is constituted as a skin needle.

A skin needle manufacturing apparatus according to the invention comprises a base installation member configured to install a base on which one or more skin needles are erected, the pin member, and a moving means configured to move the base installation member and the pin member in a direction in which the base installation member and the pin member relatively move away from each other. The moving means can move only one of or both of the base installation member and the pin member. The base installation member and the pin member are pulled away from each other by the moving means in a state in which the molten material of the needle adheres to the pin member and the base. Thus, the material can be drawn out.

The dissolution of the material of the needle is performed by adjusting the material to a predetermined temperature while the material is heated by the heat generating means. The adjustment of temperature by the heat generating means can adjust the material of the needle to a molten state having viscosity that is appropriate for drawing out the material of the needle. The heat generating means is preferable, because not only the temperature adjustment before the drawing-out of the material but that after the drawing-out of the material can be performed. The heat generating means is provided to be able to adjust the temperature of at least one of the adhesion portion adhering to the pin member and the projection portion erected on the base as a preferable configuration. For example, the heat generating means can be constituted as a base heating means configured to heat the base installation member, at which the base is installed, to thereby adjust the projection portion at the base side between the drawn-out materials to a predetermined temperature. Also, the heat generating means can be constituted as a pin heating means configured to heat the pin member to thereby adjust the adhesion portion at the pin member side between the drawn-out materials to a predetermined temperature. More preferably, to adjust the temperature of all of the drawn-out materials or a part of the drawn-out materials if necessary, both the base heating means and the pin heating means can be constituted as the heat generating means.

The material of the needle, which is in a molten state, can be discharged from the needle point portion of the pin member to the base. The pin member is a hollow pin having a fine hole provided therein. The pin member is constituted so that the molten material is discharged to the base. Consequently, the needles and the base can be formed of different materials, respectively. The needle material discharged from an end (or a fine hole of the hollow pin) in a state, in which the material adheres to the end of the pin member, adheres also to the base. In a state in which the material of the needle adheres to the pin member and the base, the pin member and the base are pulled away from each other to thereby draw out the material adhering thereto. Because the materials of the needle and the base differ from each other, an amount of the used material of the needle can be suppressed. Additionally, the material can effectively be used. In one of statuses of use of the skin needle, the stabbed needle is left in skin, while only the base is removed therefrom. In a case of using the skin needle in such a status, the degree of attachment between the needle and the base is adjusted so that the needle can easily be detached from the base. Conversely, in a case where it is intended to increase the degree of the attachment therebetween, when the material mainly composed of biodegradable substances is used as the material of the needle, it is useful that the surface of the base, on which the needle is erected, has hydrophilicity or adhesion. Particularly, the base, whose surface has adhesion, can use an adhesive force for applying the base to skin.

In a case where the pin member is a hollow pin, it is useful that the skin needle manufacturing apparatus has a container which accommodates a molten material, and a pressure control means which causes the container to discharge the accommodated material from the fine hole. The pressure control means controls pressure acting on the material accommodated in the container (e.g., the pressure of air enclosed in the container together with the material, and a piston pressure due to an external force). The material of the needle can be discharged from the hollow pin while a discharge rate is easily and smoothly adjusted by the pressure control means. Particularly, in the case of simultaneously forming a plurality of needles by arranging a plurality of hollow pins in parallel with one another, the discharge rate, at which the material is discharged from each of the hollow pins, can easily be uniformized. Also, the container heating means configured to heat the container and to adjust the material accommodated in the container to a predetermined temperature can be provided (as one of the heat generating means) to melt the material accommodated in the container and maintain a molten state.

In the case of using the hollow pin as the pin member, the skin needle manufacturing apparatus includes the moving means for drawing the pin member and the base installation member away from each other, the pressure-control means for discharging the material of the needle accommodated in the container from the pin member, the heat generating means which adjusts the temperature of the material of the needle, and control means for controlling the moving means, the pressure-control means, and the heat generating means. Each of these means is operated by the control means, so that the needle can be formed. Consequently, the effort of a worker operating the apparatus can be saved. Accordingly, the skin needle can more easily be manufactured.

The base can be formed of the material of the needle, and the needle can be formed by melting at least a part of the base as another method of forming the skin needle without using the hollow pin and the pressure control means. In this case, on condition that when the pin member is put into contact with the base, the material of a part of the base, which is put into contact with the pin member, is melted, the molten material adheres to the pin member and is drawn out of the base when the pin member and the base start being drawn away from each other. When the pin member and the base are further drawn away from each other in this state (i.e., a state in which the molten material adheres to the pin member and the base), the material is going to be drawn out. In this case, the needle and the base are integrated with each other. Thus, the degree of coupling the needle and the base can be high. Consequently, the needle and the base can be constituted so that the needle cannot easily be detached from the base.

To suppress an amount of use of the material of the needle, the material of the needle can be held at a part of the base, at which the needle is provided. Additionally, the needle can be formed of the material held at the base. A method of forming the needle is similar to the method in the case of forming the entire base of the material of the needle.

The pin member can be configured so that the shape of an end surface of the pin member, with which the material is in contact, is substantially a sphere, a circle, or a regular polygon. With this configuration, the skin needle manufacturing apparatus according to the invention can easily manufacture a skin needle having a cross-section which is substantially perpendicular to a direction of length thereof and which is substantially circularly-shaped.

Also, the pin member can be configured so that the shape of an end surface of the pin member, with which the material is in contact, is substantially a rectangle. With this configuration, the skin needle manufacturing apparatus according to the invention can easily manufacture a skin needle having a cross-section which is substantially perpendicular to a direction of length thereof and which is substantially elliptically-shaped.

The skin needle manufacturing apparatus includes the moving means for drawing the pin member and the base installation member away from each other regardless of the shape of the pin member, the heat generating means which adjusts the temperature of the material of the needle, and control means for controlling the moving means and the heat generating means. Each of these means is operated by the control means, so that the needle can be formed. Consequently, the effort of a worker operating the apparatus can be saved. Accordingly, the skin needle can more easily be manufactured.

According to the invention, before the molten material of the needle is drawn out, the material should be attached to the pin member and the base. To more surely attach the material, in a state in which the pin member and the base are at least in contact with the material of the needle, the base and the pin member are approached by a predetermined amount. According to the manufacturing apparatus of the invention, the control means controls, before the material is drawn out, the moving means in a state, in which the pin member and the base are in contact with the material, to cause the base installation member and the pin member to approach each other by a predetermined amount. Consequently, the material of the needle can more surely be attached to the pin member and the base. Particularly, in the case of simultaneously forming a plurality of needles by arranging a plurality of hollow pins in parallel with one another, all of a plurality of needles can surely be attached to the material.

After the molten material of the needle is attached to the pin member and the base, the material starts being drawn out. When the material is drawn out, the drawing-out of the base and the pin member is performed in stages. Consequently, the certainty of forming the needle can be enhanced. According to the manufacturing apparatus of the invention, the control means alternately repeats, when the material is drawn out, an operation and a stoppage of the moving means in stages. The drawing-out of the molten material is a deformation of the material, which follows the movement of drawing the base and the pin member away from each other. Accordingly, there is a delay in following the movement, the material is torn into two halfway through drawing out. A needle having a desired shape cannot be formed. The deformation of the molten material varies due to irregular factors, such as the adhesion of the material and the degree of attachment between the pin member and the base, every time the needle is formed. According to the invention, when the molten material is drawn out, after the molten material is drawn out by the moving means and the heat generating means, the control means once stops an operation of the moving means (i.e., the distance between the pin member and the base is maintained at a constant value) by further drawing the base installation member and the pin member away from each other. Thus, the apparatus is configured so that the deformation of the material surely follows the movement during the stoppage. Consequently, a control operation for forming especially micro-needles is easy to perform. Accordingly, a needle having a desired shape can more surely be formed. A time period, for which the moving means is stopped, is a time period during which the deformation of the material surely follows the movement.

When the adhesion portion having adhered to the pin member and the projection portion having adhered to the base between those of the material are separated from each other after the material is drawn out, the projection portion is obtained as a needle. The separation between the adhesion portion and the projection portion can be performed by, for example, forcibly cutting off between the adhesion portion and the projection portion with a blade-like member. Alternatively, the separation therebetween can be performed by further drawing out the material and then utilizing the fact that the drawn-out material reaches a drawing-out limit and is divided, instead of forcible cutting-off. The following method is performed as a more preferable method. That is, after the material is drawn out, the distance between the base and the pin member is maintained to lower the temperature of a separating portion of the material and to increase the adhesion thereof. Then, the base and the pin member are further drawn away from each other. Thus, the adhesion portion can be cut off from the pin member. Consequently, the adhesion portion is separated from the projection portion. According to the manufacturing apparatus according to the invention, the control means stops an operation of the moving means for a predetermined time. Then, the control means causes the moving means to further draw the base installation member and the pin member away from each other. Thus, the projection portion is separated from the adhesion portion. The separating portion of the material is extremely thin, after the material is drawn out. Consequently, the separating portion is easy to be cooled, and the withstand load of the cooled material is low, as compared with the remaining portions. Therefore, in a case where a drawn-out state of the material is maintained for a predetermined time, the separating portion is cooled by, for example, natural cooling. Also, the adhesion of the separating portion increases. In a case where the pin member and the base are drawn away from each other to further draw out the material in this state, the material is divided at the separating portion. Consequently, a needle having a desired shape can relatively easily be formed, without using the forcible cutting means. Also, in a case where the separation between the pin member and the base at that time is performed at a speed higher than that in the conventional case, the reliability of the separation can be enhanced.

More preferably, in a case where the distance between the case and the pin member is maintained for a predetermined time, an operation of the heat generating means is further operated. Alternatively, the set temperature is lowered. According to the manufacturing apparatus of the invention, the control means controls the heat generating means in such a manner. Consequently, the heat generating means for adjusting the temperature of the material halfway through drawing out the material does not impede the cooling of the separating portion of the material. Accordingly, the separation therebetween can more reliably be achieved.

The skin needle can be formed into a shape having an expanded portion radially expanded between the root of the needle and the needlepoint portion, in addition to a general shape in which the skin needle is tapered toward a direction from the root of the needle to the needlepoint portion. The shape having the expanded portion can increase the volume of the needle, as compared with the general shape. Also, the needle of the shape having the expanded portion is liable to break at a constricted part at the root side of the expanded portion. Thus, even in a case where the base is removed after the needle is stabbed into skin, the needle having the expanded portion is apt to be left in the skin.

To form a needle into a shape having the expanded portion, according to the invention, when the molten material is drawn out, the base and the pin member are once approached halfway through drawing the pin member and the base away from each other. According to the manufacturing apparatus of the invention, the control means controls and operates the moving means to once approach the base installation member and the pin member. Consequently, the pin member and the base are moved in a direction opposite to a direction, in which the pin member and the base are drawn away from each other, halfway through drawing out the material. Thus, the compressed material expands in a (radial) direction perpendicular to a drawn-out direction, so that an expanded portion is formed. Subsequently, even when the material is further drawn out, the expanded portion remains. Thus, a needle having an expanded portion can be formed.

In addition, the following method is performed as a method of forming the expanded portion into a shape having an expanded portion. That is, an operation of drawing the base and the pin member away from each other is temporarily stopped, and a stopped state is maintained so that a part of the adhesion portion or the projection portion of the material moves in a direction opposite to a direction, in which the material is drawn out, due to an own weight thereof, instead of once approaching the pin member and the base. At that time, according to the manufacturing apparatus of the invention, an operation of the moving means is stopped by the control means. Consequently, a part of the adhesion portion or the projection portion, which moves due to an own weight, constitutes the expanded portion. Subsequently, even when the material is further drawn out, the expanded portion remains still, a needle having the expansion portion can be formed.

Further, in a case where a hollow pin is used as the pin member, when the material is drawn out, the apparatus further discharges the material molten from an end portion (or the fine hole of the hollow pin) of the pin member halfway through drawing the base and the pin member away from each other. In the manufacturing apparatus of the invention, the control means operates the pressure control means. Thus, the material is further discharged from the end portion of the pin member. The newly discharged material is pushed out in a direction, in which the adhesion portion adhering to the pin member is drawn out, to thereby form an expanded portion. In a case where the material is discharged halfway through drawing out the material, a needle having the expansion portion can be formed.

It is useful that the skin needle manufacturing apparatus according to the invention is configured to further comprise humidity maintaining means which maintains humidity around the material at a predetermined value or less. Consequently, even in the case of a material that is easily melted in moisture in the air, needles can be manufactured with good accuracy.

A second-stage skin needle made of a second material at a needlepoint portion of the first-stage needle is additionally formed at the needlepoint portion of the skin needle manufactured according to the invention. Thus, a two-stage skin needle having two stage needles provided in an axial direction can be manufactured. That is, this two-stage skin needle is obtained by employing the skin needle, which is manufactured by drawing out the material using the pin member, as a first-stage needle and by forming the second-stage needle at the needlepoint portion. When the two-stage skin needle is stabbed into skin, the second stage needle is inserted into a sufficiently inner part of the skin, as compared with the first-stage needle. Therefore, the two-stage skin needle can effectively inject functional materials, which are included in the material of the second-stage needle, into skin.

The two-stage skin needle manufacturing apparatus configured to manufacture a two-stage skin needle having two-stage needles provided in an axial direction comprises a base holding member configured to hold a base, on which the first-stage needle is erected, a material installation member at which the second material is installed, and second moving means configured to move at least one of the base holding member and the material installation member in a direction in which the base holding member and the material installation member relatively move away from each other. When the second moving means draws the base holding member and the material installation member away from each other (i.e., the first-stage needle and the material installation member are drawn away from each other), in a state in which the second material is melted and adheres to the needlepoint portion, the molten second material is drawn away. Thus, the second-stage skin needle can be formed. Even in a case where a plurality of first-stage needles are provided in parallel, this manufacturing apparatus can form the second-stage needle corresponding to each of the first-stage needles.

This two-stage skin needle manufacturing apparatus may further comprises second heat generating means configured to adjust the second material to a predetermined temperature by heating the material installation member, and second control means configured to control the second heat generating means and the second moving means. This control means operates each of the second heat generating means and the second moving means to form the second-stage skin needle. Consequently, the effort of a worker operating the apparatus can be saved. Also, the two-stage skin needle can more easily be manufactured.

In a case where the first-stage needle and the second-stage needle use different materials, respectively, the needles can effectively be used by appropriately preparing the ingredients of the material of each of the needles. The material of each of the first-stage needle and the second-stage needle is composed mainly of the biodegradable substances. In a case where a material further including functional substances to be injected to skin is used as the material of the second-stage needle, the functional substances can effectively be injected into the inner part of the skin without waste.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 27 is a view illustrating a needle assembly including a two-stage skin needle formed by the two-stage skin needle manufacturing apparatus shown in FIG. 26.

FIG. 28 is a view illustrating a behavior of a first-stage needle in the process of forming a second-stage needle and also illustrating an associated formed state of the second-stage needle.

DETAILED DESCRIPTION OF THE INVENTION

The invention provides a skin-needle manufacturing apparatus and method enabled to relatively easily manufacture skin needles without excessive time, effort, and cost.

Hereinafter, embodiments of a skin needle manufacturing apparatus and method according to the invention are described below by referring to the accompanying drawings.

First Embodiment

First, the configuration of a skin needle manufacturing apparatus 10 according to a first embodiment of the invention is described below. The skin needle manufacturing apparatus 10 according to the first embodiment can manufacture skin needles which are several hundreds micrometers in length. Thus, the skin needle manufacturing apparatus 10 are of the material discharge type that discharges a material for the skin needles from a tip end of the pin member to the base.

Figure 1:
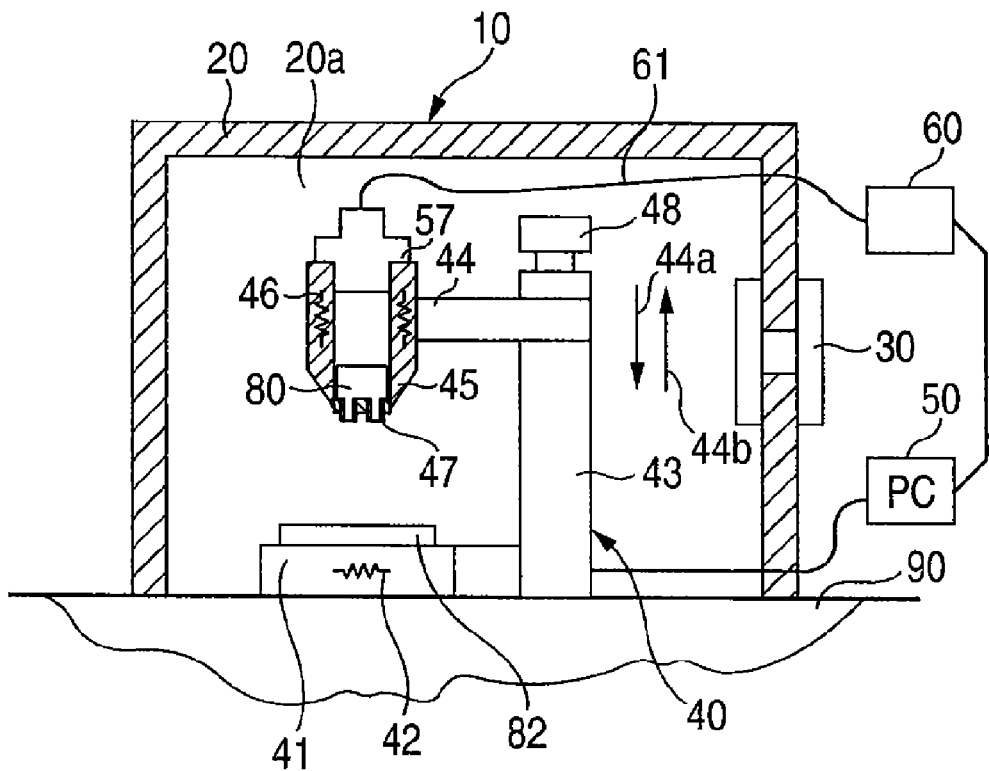
FIG. 1(a) is a side cross-sectional view of a skin needle manufacturing apparatus of the material discharge type according to a first embodiment of the invention.
FIG. 1(b) is an enlarged view of a syringe 45 of the skin needle manufacturing apparatus.
Figure 1:
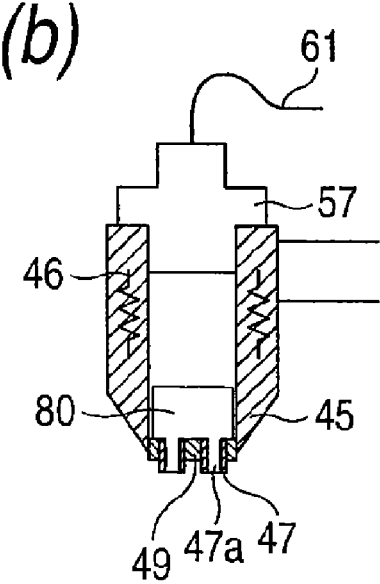
Figure 2:
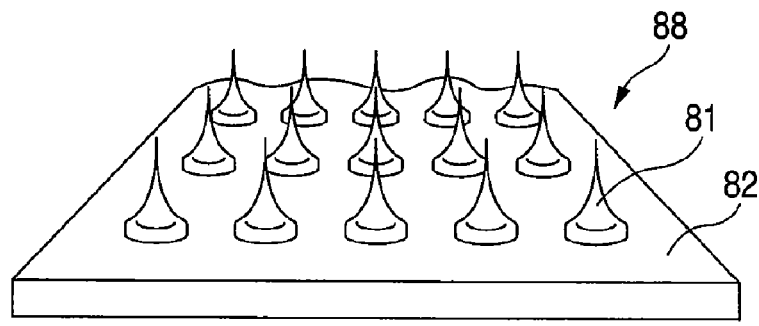
FIG. 2 is a partial appearance perspective view of a needle assembly including a plurality of skin needles manufactured by the skin needle manufacturing apparatus illustrated in FIG. 1.
Figure 3:
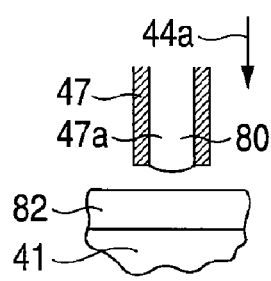
FIGS. 3(a)-3(d) illustrated the behavior of a pin member in the process of forming the skin needle and also illustrating an associated state of the material.
Figure 3:
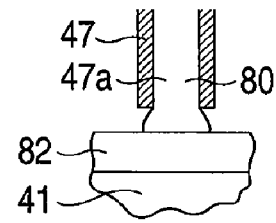
Figure 3:
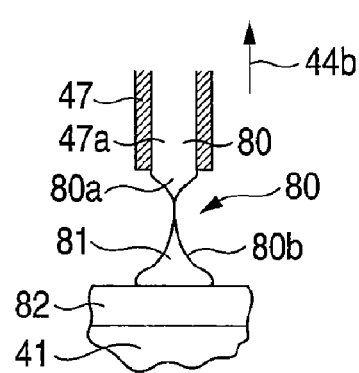
Figure 3:
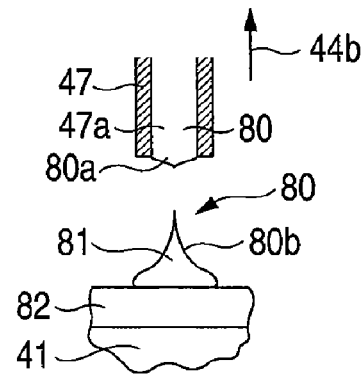

As illustrated in FIG. 1(a), the skin needle manufacturing apparatus 10 according to the first embodiment has a wall portion 20 as an outer case. The wall portion 20 is installed on a pedestal 90. A chamber 20a is formed in the wall portion 20. A humidity maintaining means 30, which maintains the inner humidity of the chamber 20a within a predetermined range (i.e., a range between 30% and 60% and between ±5% of a set humidity), is installed in the wall portion 20. A body 40 of the skin needle manufacturing apparatus 10. The body 43 has a pillar portion 43 erected on the pedestal 90, a base installation member 41 disposed at root of the pillar portion 43, a moving portion 44 upwardly and downwardly movably (i.e., in directions respectively designated by arrows 44a and 44b in the figure) supported on the pillar portion 43, a drive mechanism 48 serving as the moving means for moving the moving portion 44 along the pillar portion 43, and a computer 50 serving as control means configured to control an operation of the drive mechanism 48, as major components. FIG. 2 is a partly appearance perspective view of a needle assembly 88 including a skin needle 81 manufactured by the skin needle manufacturing apparatus 10.

The base installation member 41 is installed on the pedestal 90. A base 82, on which the skin needle 81 is erected, is installed on the top surface of the base installation member 41. The moving portion 44 is positioned above the base installation member 41. The moving portion 44 has a syringe 45 serving as a container, which accommodates a material 80 of the skin needle 81 and is placed at a position facing the top surface of the base installation member 41. FIG. 1(b) is a partial enlarged view of the syringe 45 shown in FIG. 1(a). A plurality of pin members 47 extending to the base installation member 41 are provided at the bottom portion of the syringe 45. Each of the pin members 47 is a hollow pin having a fine hole 47a provided therein. The material 80 accommodated in the syringe 45 is discharged from the fine hole 47a. Also, there is an arrangement of 10 rows by 5 columns, for a total of 50 pin members 47 corresponding to grid positions, which are provided in parallel at intervals of about 500 μm. Each of the pin members 47 is formed of a highly thermally conductive metal (e.g., brass). A cap 57 configured to hold an internal pressure of the syringe 45 is attached to the top end portion of the syringe 45. A tube 61 extending from the cap 57 to a pressure control means 60 provided outside the chamber 20a. The pressure control means 60 controls a pressure acting on a piston (not shown), which presses the material 80 in the syringe 45 by sending compressed air through the tube 61 into the syringe 45 thereby to control the discharge of the material 80 from the fine hole 47a of each of the pin member 47. Incidentally, in FIG. 1, only two pin members 47 are drawn, for simplicity of drawing, and for ready understanding.

The body 40 of the apparatus has a base heating means 42 provided in the base installation member 41, a pin heating means 49 attached to the pin member 47, and a container heating means 47 attached to the syringe 45 as the heat generating means for adjusting the material 80 to a predetermined temperature. The base heating means 42 heats the base installation member 41 and adjusts the temperature of the material 80 installed on the top surface of the base installation member 41 (particularly, the base heating means 42 adjusts the temperature of the material 80 adhering to the base 82 in addition to the temperature of the base 82 installed on the base installation member 41). On the other hand, the pin heating means 49 heats the pin member 47 and adjusts both the material 80 placed in the fine hole 47a of the pin member 47 and the material 80 adhering to an end portion of the pin member 47 after discharged from the fine hole 47a. The container heating means 46 heats the syringe 45 and adjusts the temperature 80 accommodated in the syringe 45. These heat generating means (i.e., the base heating means 42, the pin heating means 49, and the container heating means 46) are controlled, together with the drive mechanism 48 serving as the moving means, by the computer 50.

The drive mechanism 48 includes an electric motor provided therein. A revolving motion of the electric motor is converted into a rectilinear motion by a rack-and-pinion mechanism and causes the moving portion 44 to upwardly and downwardly move along the pillar portion 44. The drive mechanism 48 moves the syringe 45 and the pin member 47 fixed to the moving portion 44 with respect to the base 82 installed on the base installation member 41 by moving the moving portion 44 upwardly and downwardly. The drive mechanism 48 constitutes the moving means.

According to the present embodiment, a material employing biodegradable substances (e.g., maltose (or malt sugar) and polylactic acid) as major ingredients and including functional substances to be injected into skin is used as the material 80 of the skin needle 81 accommodated in the syringe 45. A sheet of paper or tape, a plastic sheet, or a metallic sheet having heat resistance and contractility as the material of the base 82, on which the skin needle 81 is erected, according to the purpose of the skin needle 81.

Figure 4:
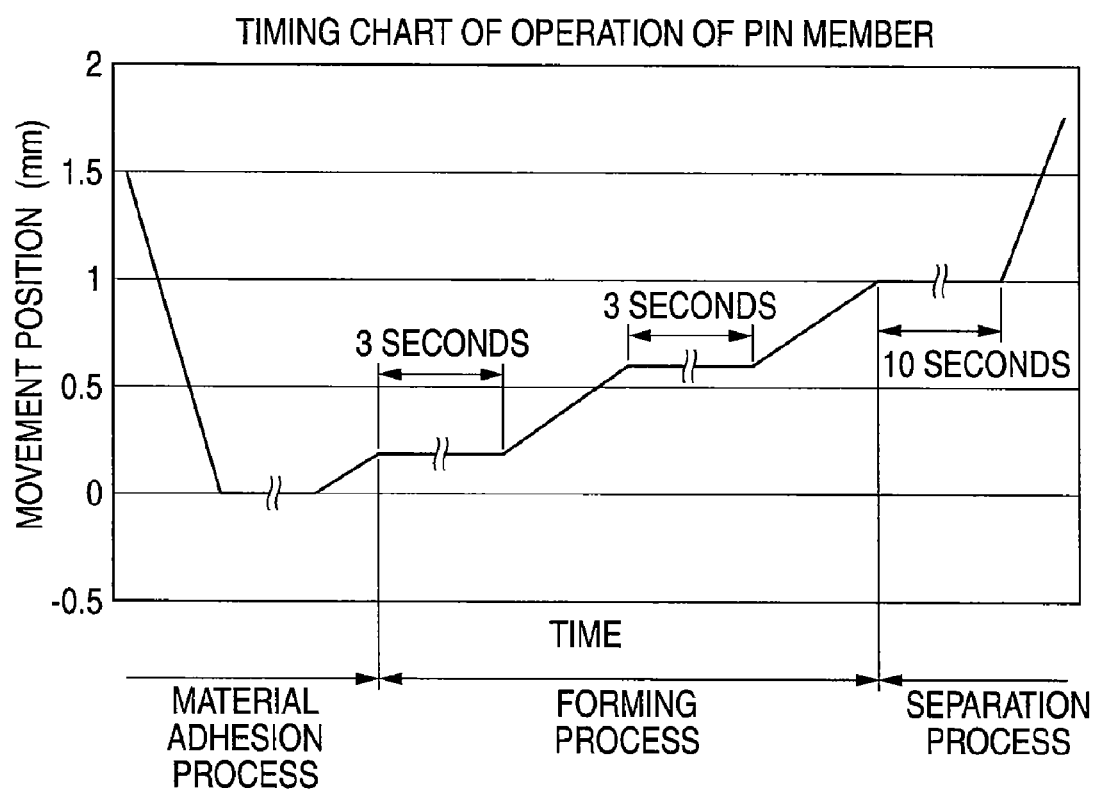
FIG. 4 is a timing chart illustrating a moving state of the pin member in the process of forming the skin needle.

An operation of the skin needle manufacturing apparatus of the material discharge type is described below in the order of steps of a manufacturing process. FIGS. 3(a) to 3(d) are view illustrating the movement of the pin member 47 in each of the steps and an associated discharged state of the material 80. Further, FIG. 4 is a timing chart illustrating the moving state of the pin member 47 in each of the steps. Incidentally, a humidity maintaining unit 30 is set so that the internal humidity of the chamber 20a is equal to or more than 30%.

1-1: Material Melting Step

First, as a needle manufacturing preparation stage, the base 82, on which the skin needle 81 is erected, is installed on the top surface of the base installation member 41. When a signal instructing the manufacture of the skin needle 81 is input to the computer 50, the computer 50 operates the container heating means 46 and the pin heating member 49 and melts the material 80 accommodated in the syringe 45. A heating temperature to which the container and the pin are heated by the container heating means 46 and the pin heating means 49, is set at about 120° C.

1-2: Material Adhesion Step

Next, the computer 50 operates the base heating means 42 to heat the base installation member 41. Consequently, the base 82 installed on the top surface of the base installation member 41 is heated. The heating temperature, to which the base 82 is heated by the base heating means 42, is set at about 100° C. Subsequently, the computer 50 operates the drive mechanism 48 and causes the moving portion 44 to move along the pillar portion 43 in a downward direction (i.e., a direction designated by arrow 44a). Consequently, the syringe 45 fixed to the moving portion 44 moves downwardly to approach the base 82 installed at the base installation member 41. The computer 50 moves down the moving portion 44 to a position at which the gap between an end of the pin member 47 placed at the bottom of the syringe 45 and the base 82 is about 500 μm. Additionally, the computer 50 causes the moving portion 44 to hold the position (see FIG. 3(a)). In a state in which this position of the moving portion 44 is held, the computer 50 operates the pressure control means 60 and sends compressed air to the syringe 45 through the tube 61. Then, a part of the material 80 in the syringe 45 is discharged from the fine hole 47a of the pin member 47. The discharged material 80 adheres to the base 82 (see FIG. 3(b)). Consequently, the material 80 is put into a state in which the material 80 adheres to the pin member 47 and the base 82.

1-3: Forming Step

Next, the computer 50 operates the drive mechanism 48 and causes the moving portion 44 to move along the pillar portion 43 upwardly (i.e., in a direction designated by arrow 44b). With this movement, the pin member 47 rises and is drawn away from the base 82. The material 80 adhering to both the members are drawn out by being pulled. A movement speed at that time is about 100 μm. The drawn-out material 80 is divided into the adhesion portion 80a adhering to the pin member 47 and the projection portion 80b adhering to the base. The projection portion 80b is projected by a tensile force generated between the base and the adhesion portion 80a provided at the side of the pin member 47 to be tapered toward an upward direction. With this, the adhesion portion 80a is tapered toward a downward direction. In a case where an operation of drawing out the material is further performed, the connection portion between the adhesion portion 80a and the projection portion 80b becomes extremely thin, before long (see FIG. 3(c)).

In this forming process, both the pin heating means 49 and the base heating means 42 operate to heat the material 80 and to continue to adjust the material 80 to a predetermined temperature. The pin heating means 49 heats the pin member 47 thereby to adjust the adhesion portion 47a of the material 80, which adheres to the pin member 47. On the other hand, the base heating means 42 heats the base installation member 41 to thereby adjust each of the base 82, to which the material 80 adheres, and the projection portion 80b erected on the base 82 to a predetermined temperature. The material 80 of the needle is adjusted by the two heat generating means, which are the base heating means 49 and the pin member 47, to a molten state in which the material 80 has adhesion suitable for being drawn out.

As illustrated in a timing chart shown in FIG. 4, the computer 50 alternately repeats operating and stopping the drive mechanism 48 to thereby lift the pin member 47 in stages. The pin member 47 is drawn away from the base installation member 41 in stages. Thus, the deformation of the material 80 to be drawn out can easily follow an operation of drawing the pin member 47 away from the base installation member 41. Consequently, a needle having a desired shape can more reliably be formed. In this embodiment, the computer 50 operates the drive mechanism 48 to upwardly move the pin member 47 by 200 μm. Subsequently, the computer 50 temporarily stops the operation of the drive mechanism and maintains the pin member 47 at the position. A time period, during which the operation of the drive mechanism 48 is temporarily stopped, is about 3 seconds. Subsequently, the computer 50 controls the drive mechanism 48 again and moves the pin member 47 upwardly by 400 μm. Thereafter, the computer 50 causes the pin member 47 to maintain the position by 3 seconds. When the pin member 47 moves upwardly by 400 μm after this stoppage thereof, the material 80 is sufficiently drawn out. The connection portion between the adhesion portion 80a and the projection portion 80b is put into a state shown in FIG. 3(c), in which the connection portion therebetween is extremely thin. A total rise distance of the pin member 47 is 1000 μm. The height (or axial length) of the projection portion 80b is approximately 500 μm. Also, the projection portions 80b, i.e., a grid-point arrangement of 10 rows by 5 columns, for a total of 50 projection portions 80b are erected on the top surface of the base 82 corresponding to a plurality of pin members 47, respectively.

1-4: Separation Step

Upon completion of drawing out the material 80 in the forming step, the computer 50 stops an operation of the drive mechanism 48 for a predetermined time period (in this case, about 10 seconds) to thereby maintain a state in which the material 80 is drawn out. During this stoppage time period, the connection portion between the adhesion portion 80a and the projection portion 80b of the material 80 is cooled by natural heat radiation. Thus, the adhesion of the connection portion is increased. Subsequently, the computer 50 operates the drive mechanism 48 and causes the moving portion 44 to move upwardly (i.e., in a direction designated by arrow 44b). Then, the pin member 47 is further drawn away from the base installation member 41, so that the adhesion portion 80a adhering to the pin member 47 is separated from the projection portion 80b by employing the connection portion as a boundary. The rising movement speed of the pin member 47 is higher than the speed of the movement in the forming step and is about 5 mm/second. Consequently, the projection portion 80b is formed as the skin needle 81 (see FIG. 3(d)). Also, the apparatus can be configured so that heat radiation of the material 80 is less prevented by stopping an operation of the heat generating means, such as the pin heating means 49 and/or the base heating means 42, in the separation step.

As described above, the skin needle manufacturing apparatus 10 can manufacture the skin needle 81 directly on the base 82, as illustrated in FIG. 2. Incidentally, the adhesion portion 80a remains attached to the pin member 47 can be drawn back to the syringe 45 by causing the pressure control mechanism 60 to reduce the internal pressure of the syringe 45 through the tube 61. The drawn-back adhesion portion 80a can be used as the material 80 of the skin needle which will be next manufactured.

Figure 5:
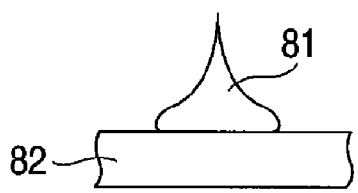
FIG. 5(a) is a side view of a skin needle formed by shaping a fine hole of the pin member substantially like a circle.
FIG. 5(b) is a top view thereof.
Figure 5:
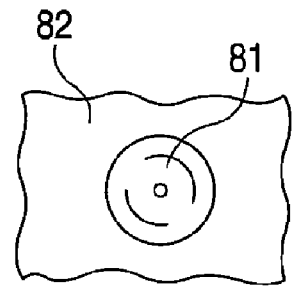
Figure 6:
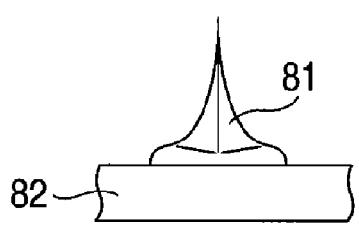
FIG. 6(a) is a side view of a skin needle formed by shaping a fine hole of the pin member substantially like a triangle.
FIG. 6(b) is a top view thereof.
Figure 6:
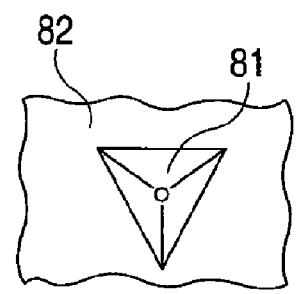
Figure 7:
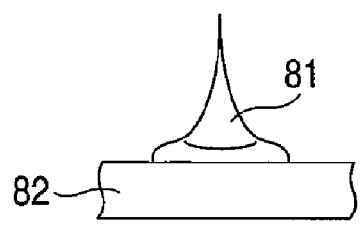
FIG. 7(a) is a side view of a skin needle formed by shaping a fine hole of the pin member substantially like a quadrangle.
FIG. 7(b) is a top view thereof.
Figure 7:
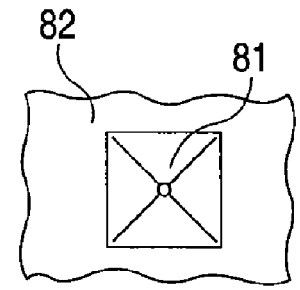
Figure 8:
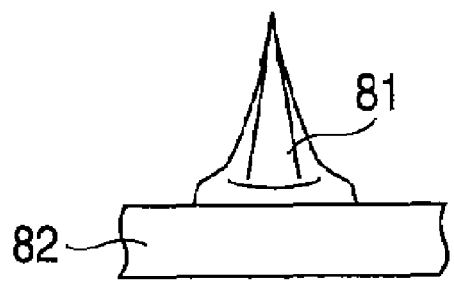
FIG. 8(a) is a side view of a skin needle formed by shaping a fine hole of the pin member substantially like a hexagon.
FIG. 8(b) is a top view thereof.
Figure 8:
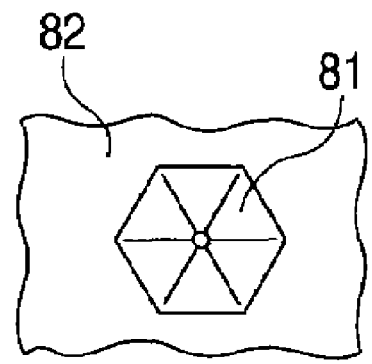

Incidentally, in a case where the fine hole 47a, from which the material 80 is discharged, in the pin member 47 is cross-sectionally substantially circularly-shaped, the skin needle manufacturing apparatus 10 can manufacture a substantially conically-shaped skin needle 81, as illustrated in FIG. 5. In a case where the fine hole 47a is cross-sectionally substantially triangularly-shaped, the skin needle manufacturing apparatus 10 can manufacture a skin needle 81 shaped substantially like a trigonal pyramid, as illustrated in FIG. 6. In a case where the fine hole 47a is cross-sectionally substantially quadrangularly-shaped, the skin needle manufacturing apparatus 10 can manufacture a skin needle 81 shaped substantially like a quadrangular pyramid, as illustrated in FIG. 7. In a case where the fine hole 47a is cross-sectionally substantially hexagonally-shaped, the skin needle manufacturing apparatus 10 can manufacture a skin needle 81 shaped substantially like a hexagonal pyramid, as illustrated in FIG. 8. It can easily be presumed that the skin needle manufacturing apparatus 10 can manufacture a skin needle 81 having a shape in which the shape of the fine hole 47a is reflected.

Figure 9:
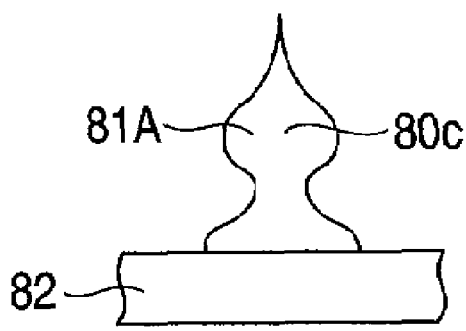
FIG. 9(a) is a side view of a skin needle having an expanded portion.
FIG. 9(b) is a top view thereof.
Figure 9:
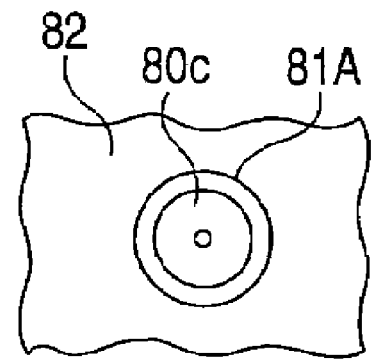
Figure 10:
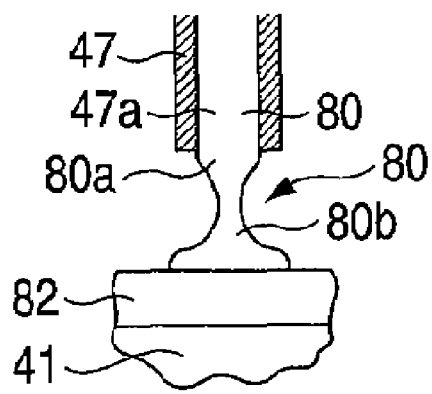
FIG. 10 is a view illustrating the behavior of a pin member in the process of forming the skin needle having the expanded portion and also illustrating an associated state of the material.
Figure 10:
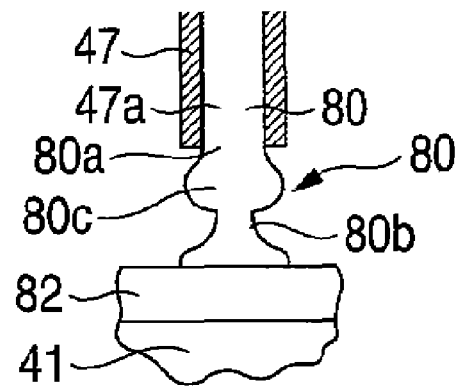
Figure 10:
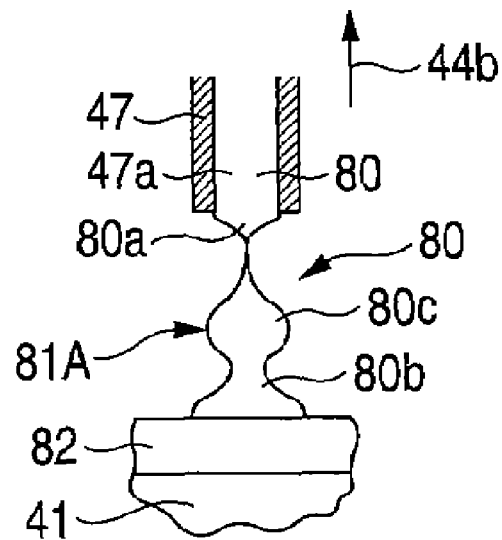

In the sequence of steps, a skin needle 81 having a general tapered shape (i.e., a shape gradually tapered toward the needlepoint end from the root) can be formed. Also, the skin manufacturing apparatus 10 of the material discharge type can manufacture a skin needle 81A having an expanded portion 80c (i.e., a portion radially expanded between the root and the needlepoint end of the needle) shown in FIG. 9 by being operated in the forming step as follows. FIGS. 10(a) to 10(c) are views illustrating the skin needle 81A having the expanded portion 80c.

1-3A: Forming Step/Needle Having Expanded Portion

In the forming step, the computer 50 temporarily stops an operation of the drive mechanism 48 and maintains the position of the pin member 47 (see FIG. 10(a)) halfway through drawing the base installation member 41 and the pin member 47 away from each other to draw out the material 80. Simultaneously with this, the computer 50 operates the pressure control means 60 and sends compressed air to the syringe 45 through the tube 61. Consequently, the material 80 is discharged from the tip end of the pin member 47 provided in the syringe 45. Then, the capacity of the adhesion portion 80a adhering to the pin member 47 is increased. A lower portion of the adhesion portion 80a collides with the projection portion 80b and radially expands (see FIG. 10(b)), while pushed down. Subsequently, the computer 50 operates the drive mechanism 48 and draws out the material 80 by moving the pin member 47 upwardly (i.e., in a direction designated by arrow 44b). Thus, the skin needle 81A having an expanded portion 80c in an intermediate portion of the material 80 is formed.

The skin needle 81A having the expanded portion 80c can be increased in volume, as compared with the skin needle having a general tapered shape. Thus, a large amount of functional substances can be injected through the skin needle 81A into skin. Also, the skin needle 81A has a shape due to which the needle 81A is liable to break at a constriction portion at the side of the root of the expanded portion 81c. Thus, even when the base is removed after the needle is stabbed in skin, the needle including the expanded portion 81c is apt to be left in the skin.

The above-described skin needle manufacturing apparatus 10 of the material discharge type manufactures a skin needle 81 formed of a molten material 80 discharged from the tip end of the pin member 47. Thus, a mold as used according to the conventional technique is unnecessary. Additionally, the materials of the skin needle 81 and the base 82 can be set to differ from each other. Consequently, the material 80 of the skin needle 81 can effectively be used. Also, skin needles of various shapes can be manufactured by changing the cross-sectional shape of the fine hole 47a of the pin member 47 or changing the speed at which the pin member 47 and the base 82 are separated from each other.

Second Embodiment

A skin needle manufacturing apparatus 110 according to a second embodiment of the invention is described below. The skin needle manufacturing apparatus 10 of the material discharge type discharges the material of the needle from the tip end of the pin member 47 to the base 82. In contrast, the skin needle manufacturing apparatus 110 described below is of the material drawing-up type that forms the base of the material of the needle and that forms a needle by melting a part of the base. The skin needle manufacturing apparatus 110 of the material drawing-up type differs from that of the material discharge type basically only in the pin member 47 and peripheral devices thereof. Most of the constituent elements of the skin needle manufacturing apparatus 110 of the material drawing-up type are the same as the corresponding elements of the apparatus of the material discharge type. Therefore, the constituent elements of the skin needle manufacturing apparatus 110 of the material drawing-up type, which are the same as those of the apparatus of the material discharge type, are designated by the same reference numerals in the drawings. The detailed description of such constituent elements is omitted.

Figure 11:
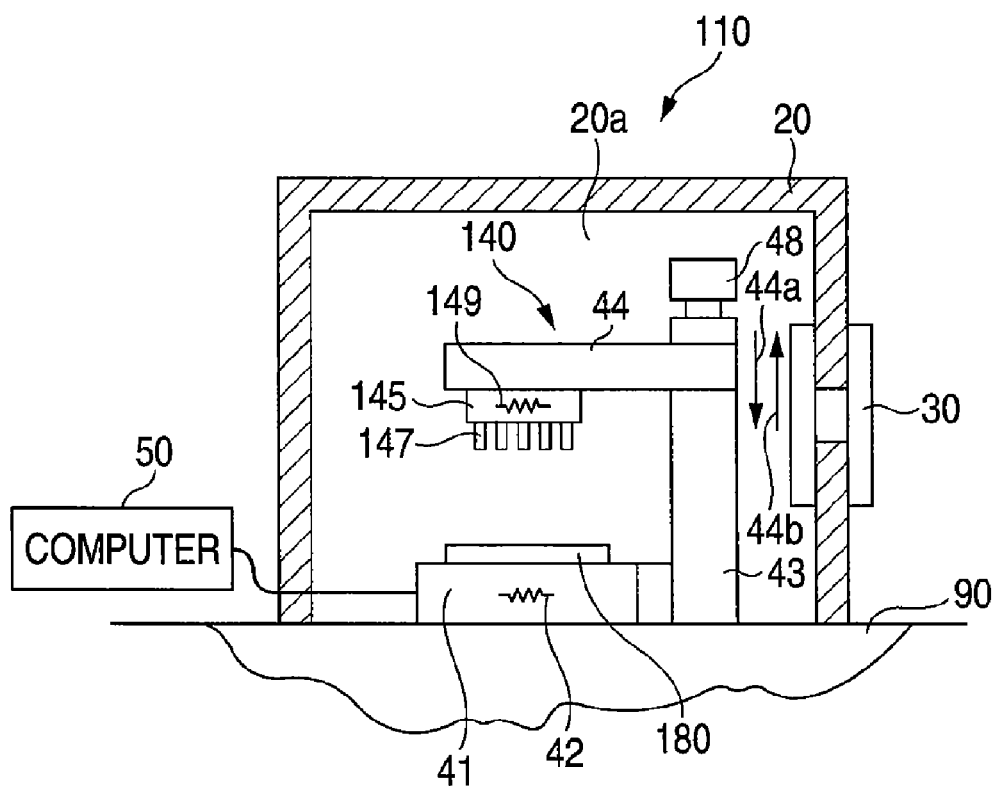
FIG. 11 is a side cross-sectional view of a skin needle manufacturing apparatus of the material drawing-up type according to a second embodiment of the invention.

As illustrated in FIG. 11, the skin needle manufacturing apparatus 110 of the material drawing-up type has a substrate 145 provided at a position facing the top surface of the material installation member 41. The substrate 145 is attached to the bottom surface of the moving portion 44 which upwardly and downwardly moves. The substrate 145 is provided with a plurality (e.g., 50 to 1000) of the pin members 147 which are used to attach a part of the material 80 to the bottom surface thereof. (The substrate 145 is a substitute for the syringe 45 of the apparatus of the material discharge type, and thus the apparatus of the material drawing-up type is not provided with the pressure control means 60 which is provided in the apparatus of the material discharge type). Each of the pin members 147 is shaped like a solid cylinder. The substrate 145 is formed so that the size and the shape of a part thereof, on which each of the pin members 147 is provided, are about 5 mm to 50 mm square and a quadrate. The pin members 147 are installed like grid points on the substrate 145 substantially at uniform intervals and are formed of a highly thermally conductive metal (e.g., brass). Incidentally, only 5 pin members are illustrated in FIG. 11 for simplicity of drawing in view of visibility.

Figure 12:
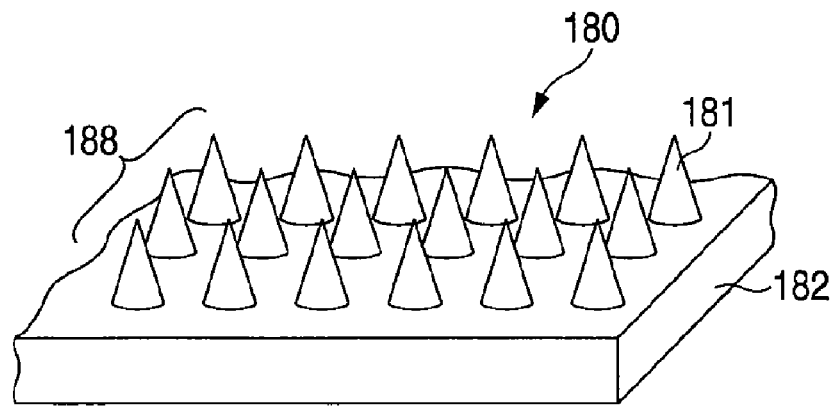
FIG. 12 is a partial appearance perspective view of a needle assembly including a plurality of skin needles manufactured by the skin needle manufacturing apparatus illustrated in FIG. 11.

FIG. 12 is a partial appearance perspective view of a needle assembly 188 including the skin needle 181 manufactured by the skin needle manufacturing apparatus 110. A material 180 is the material of the skin needle 181 and is also that of a base 182 on which the skin needle 181 is erected. The material 180 is formed of a material which employs biodegradable substances (e.g., maltose (or malt sugar) and polylactic acid) as major ingredients and is mixed with functional substances to be injected into skin. The material 180 of the skin needle is installed on the top surface of the base installation member 41.

A body 140 has a base heating means 42 provided as a heat generating means for adjusting the material 180 to a predetermined temperature in the base installation member 41, and a pin heating means 149 provided in the base installation member 41. The base heating means 42 heats the base installation member 41 and adjusts the temperature of the material 180 installed on the top surface of the base installation member 41. On the other hand, the pin heating means 149 heats the substrate 145 to thereby indirectly heat the pin member 147 and adjusts the temperature of the material 80 attached to the pin members 147. The base heating means 42 and the pin heating means 149 serving as the heat generating means are controlled, together with the drive mechanism 48 serving as the moving means, by the computer 50.

Figure 13:
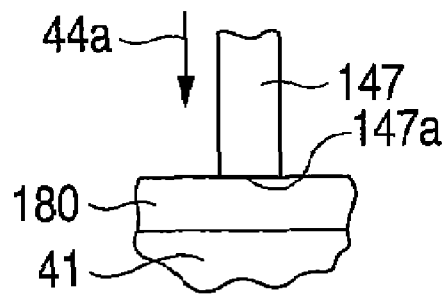
FIG. 13 is a view illustrating the behavior of a pin member in the process of forming the skin needle and also illustrating an associated state of the material.
Figure 13:
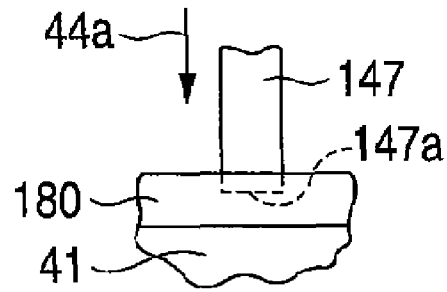
Figure 13:
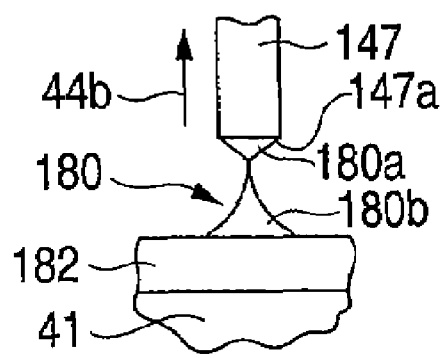
Figure 13:
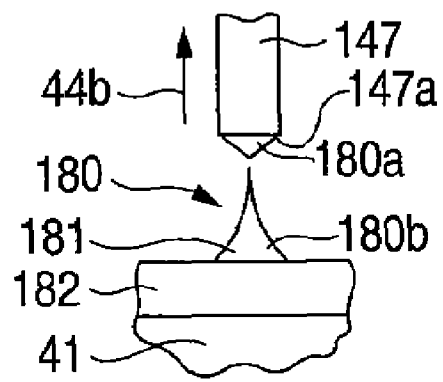
Figure 14:
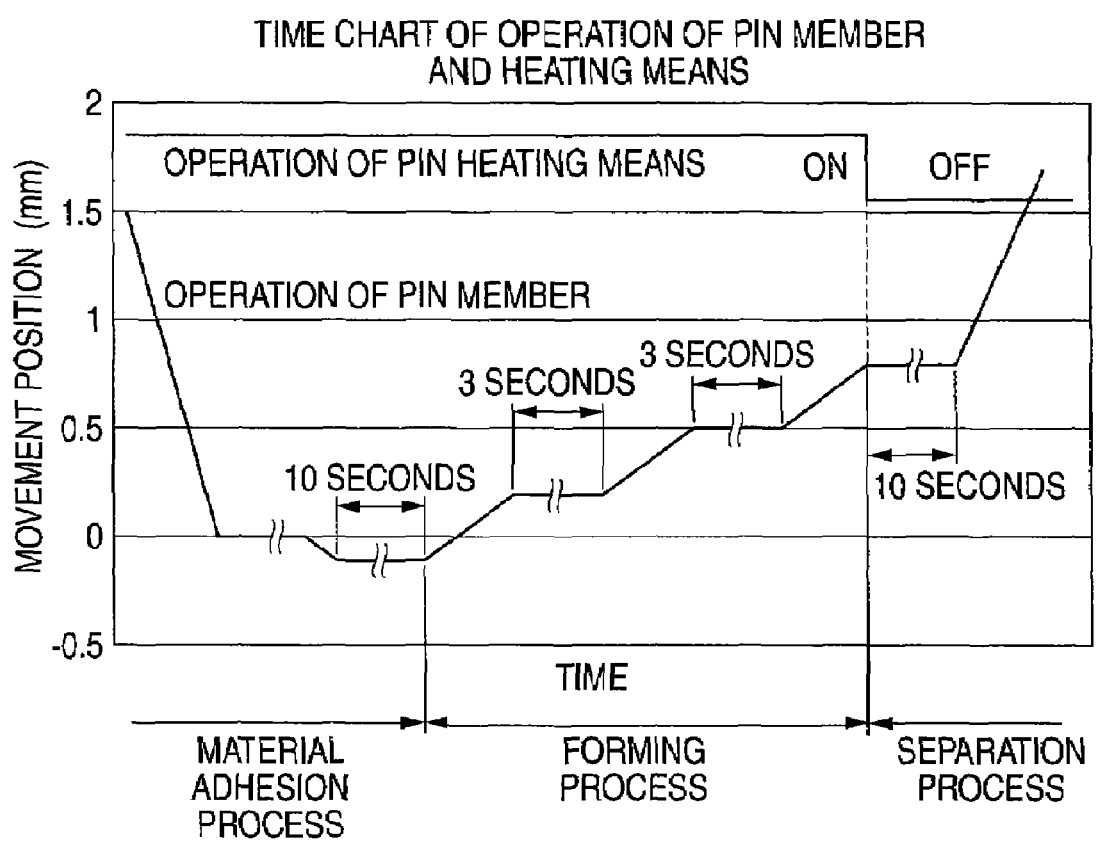
FIG. 14 is a timing chart illustrating a moving state of the pin member in the process of forming the skin needle.

Next, an operation of the skin needle manufacturing apparatus of the material drawing-up type is described below in the order of steps of a manufacturing process of manufacturing the skin needle 181. FIG. 13 is a view illustrating the movement state of the pin member 147 in each of steps (from a material adhesion step to a separating step) and an associated state of the material 180. Further, FIG. 14 is a timing chart illustrating the moving state of the pin member 147 in each of the steps (from the material adhesion step to the separating step).

2-1: Material Melting Step

First, as a needle manufacturing preparation stage, the material 180 of the skin needle 181 is installed on the top surface of the base installation member 41. When a signal instructing the manufacture of the skin needle 181 is input to the computer 50, the computer 50 sets a heating temperature at which the base installation member 41 is heated by the base heating means 42, at about 120° C. Then, the computer 50 causes the base heating means 42 to melt the material 180 installed on the base installation member 41. Upon completion of melting the material 180, the computer 50 sets a heating temperature, at which the base is heated by the base heating means 42, at about 100° C. In the next step or later, the set temperature of 100° C., at which the base is heated by the base heating means 42, is maintained.

2-2: Material Adhesion Step

Next, the computer 50 operates the pin heating means 149 to heat the pin members 147. A heating temperature at which the pin members are heated by the pin heating means 149 is set at about 120° C. Heating by the pin heating means 149 is maintained until the next forming step is completed.

The computer 50 operates the drive mechanism 48 and causes the moving portion 44 to move along the pillar portion 43 in a downward direction (i.e., a direction designated by arrow 44a). Then, the pin member 147 installed on the moving portion 44 through the substrate 145 approaches the material 180 melted on the base installation member 41. When an end surface 147a of the pin member 147 is brought into contact with the material 180, the computer 50 temporarily stops an operation of the drive mechanism 48 and recognizes this stopping position as a zero-point position which is a reference in movements in upward and downward directions of the pin member 147 (see FIG. 13(a)). At this zero-point position, an adhesive force acting between the pin member 147 and the material 180 may be insufficient. Particularly, a plurality of the pin members 147 are configured so that the pin members 147 are put into uniform contact with the material 180, and that the end surface 147a of each of the pin members 147 is fit in the same virtual horizontal surface. Actually, due to the machining precision of the pin members 147, wear caused by the use of the pin members 147 on one side, and the horizontal surface accuracy of the top surface of the material 180 on the other side, it is difficult to obtain such uniform contact with the material 180. Thus, the computer 50 causes each of the pin members 147 from the zero-point position to further approach the base installation member 41 by a predetermined amount (e.g., 100 μm) (see FIG. 13(b)). Consequently, each of the pin members 147 can reliably adhere to the material 180. Also, to surely obtain the attachment between the material 180 and each of a plurality of the pin members 147, each of the pin members 147 maintains the position thereof close to the base installation member 41 for a time period of, for example, 10 seconds.

2-3 Forming Step

Next, the computer 50 uses the drive mechanism 48 which causes the moving portion 44 to move upwardly (i.e., a direction designated by arrow 44b) to thereby draw the pin members 147 away from the base installation member 41. The operation of drawing the pin members away from the base installation member draws out the material 180 having adhered to the end surface 147a of the pin member 147 (see FIG. 13(c)). The drawn-out material 180 includes the adhesion portion 180a adhering to the pin members 147 and the projection portion 180b projected to upwardly be drawn up by a tensile force generated between the base and the adhesion portion 180a. The projection portion 180b is formed to be erected on the base 182 formed of the same material 180. In the forming step, both the pin heating means 149 and the base heating means 42 operate to heat the material 180 and to continue to adjust the material 180 to a predetermined temperature. The pin heating means 149 heats the pin members 147 and functions to adjust the adhesion portion 180a, which adheres to the pin member 147, in the material 180 to a predetermined temperature. The base heating means 42 on one side heats the base installation member 41 and functions to adjust the projection portion 180b erected on the base 182 to a predetermined temperature. The two heat generating means including the pin heating means 149 and the base heating means 42 adjust the material 180 of the skin needle 181 to a molten state in which the material 180 of the skin needle 181 has adhesion suitable for drawing out the material 180.

As illustrated in a timing chart shown in FIG. 4, in this forming step, the computer 50 alternately repeats operating and stopping the drive mechanism 48 thereby to draw the pin members 147 away from the base installation member 41 in stages, and to draw out the material 180. The operation of gradually drawing the pin members 47 away from the base installation member 41 in stages causes the deformation of the material 180 to be drawn out can easily follow an operation of drawing the pin member 47 away from the base installation member 41. Consequently, a needle having a desired shape can more reliably be formed. In this embodiment, first, the computer 50 operates the drive mechanism 48 to upwardly move the pin members 47 by 300 μm. Subsequently, the computer 50 temporarily stops the operation of the drive mechanism for about 3 seconds. Subsequently, the computer 50 causes the pin members 147 to further upwardly move by 300 μm. Then, the computer 50 stops an operation of the drive mechanism 48 for about 3 seconds. Subsequently, the computer 50 moves the pin member 147 upwardly by 300 μm. The speed of each of the movements is about 2 mm/second. Consequently, the pin members 147 are positioned above the zero-point position recognized by the computer 50 by 900 μm. At that time, as illustrated in FIG. 13(b), the projection portion 180b having a length of about 500 μm is formed. Incidentally, the pin members 147 are installed on the substrate 145 like grid-points substantially at uniform intervals. Thus, a plurality of projection portions 180b are formed like grid points substantially at uniform intervals corresponding to the positions of the pin members 147.

2-4 Separation Step

Upon completion of drawing out the material 180, the computer 50 stops an operation of the pin heating means 149 and an operation of the drive mechanism 48 for a predetermined time period (e.g., about 10 seconds). This stoppage time period is a time in which the connection portion (at which the adhesion portion 180a and the projection portion 180b are separated from each other) between the adhesion portion 180a and the projection portion 180b of the material 180 is cooled by natural heat radiation so that the adhesion of the connection portion can be increased. Subsequently, the computer 50 operates the drive mechanism 48 and causes the moving portion 44 to move upwardly (i.e., in the direction designated by arrow 44b). Then, the pin members 147 are further drawn away from the base installation member 41, so that the adhesion portion 180a adhering to the pin member 147 is separated from the projection portion 180b. The movement speed of the pin member 147 is higher than the speed of the movement in the forming step and is about 5 mm/second. Consequently, the projection portion 180b is formed as the skin needle 181. Incidentally, the computer 50 stops only the pin heating means 149 of the heat generating means. However, in a case where an operation of the base heating means 42 serving as the other heat generating means is additionally stopped, the apparatus can be configured so that heat radiation cooling of the material 180 is less prevented.

Figure 15:
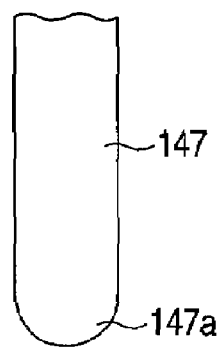
FIG. 15(a) is a side view of a skin needle formed by shaping an end surface of the pin member substantially like a sphere.
FIG. 15(b) is a bottom view thereof.
Figure 15:
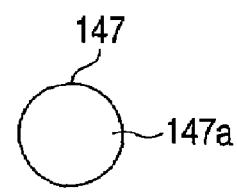
Figure 16:
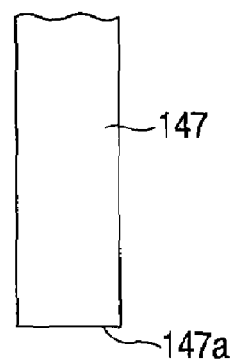
FIG. 16(a) is a side view of a skin needle formed by shaping an end surface of the pin member substantially like a circle.
FIG. 16(b) is a bottom view thereof.
Figure 16:
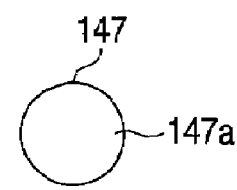
Figure 17:
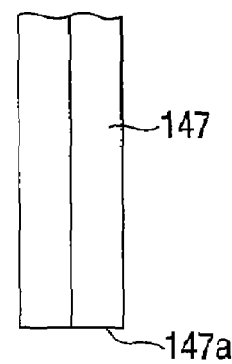
FIG. 17(a) is a side view of a skin needle formed by shaping an end surface of the pin member substantially like an equilateral triangle.
FIG. 17(b) is a bottom view thereof.
Figure 17:
Figure 18:
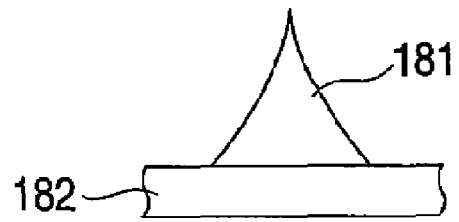
FIG. 18(a) is a side view of each of skin needles formed by the skin needle manufacturing apparatuses respectively provided with the pin members shown in FIGS. 15, 16, and 17.
FIG. 18(b) is a top view thereof.
Figure 18:
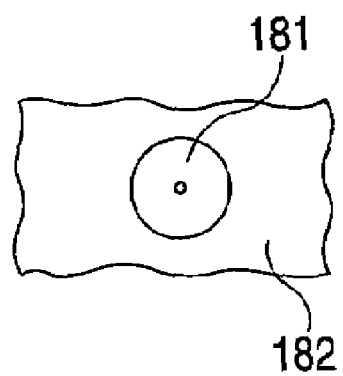
Figure 19:
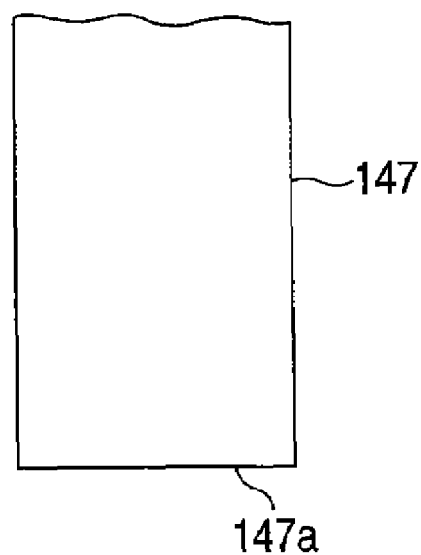
FIG. 19(a) is a side view of a skin needle formed by shaping an end surface of the pin member substantially like a rectangle.
FIG. 19(b) is a bottom view thereof.
Figure 19:
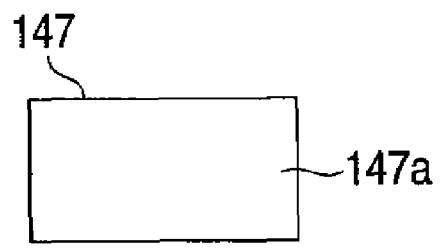
Figure 20:
FIG. 20(a) is a side view of a skin needle formed by a skin needle manufacturing apparatus having the pin member shown in FIG. 19.
FIG. 20(b) is a bottom view thereof.
Figure 20:
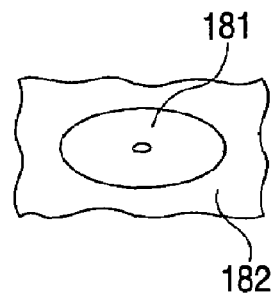

Incidentally, in a case where the fine hole 47a, from which the material 80 is discharged, in the pin member 47 is cross-sectionally substantially spherically-shaped as shown in FIG. 15 or is cross-sectionally substantially circularly-shaped as shown in FIG. 16 or is cross-sectionally substantially shaped like a regular polygon, for example, a triangle, as shown in FIG. 17, the skin needle manufacturing apparatus 110 of the material drawing-up type can manufacture a skin needle 181 having a cross-section which is substantially perpendicular to a direction of length thereof and which is substantially circularly-shaped as shown in FIG. 18. Also, in a case where the fine hole 47a is cross-sectionally substantially rectangularly-shaped as shown in FIG. 19, the skin needle manufacturing apparatus 110 can manufacture a skin needle 181 having a cross-section which is substantially perpendicular to a direction of length thereof and which is substantially elliptically-shaped as shown in FIG. 20.

In the above sequence of steps, the skin needle manufacturing apparatus 110 of the material drawing-up type can manufacture a skin needle 181 of a general shape. Additionally, the skin manufacturing apparatus 110 of the material drawing-up type can manufacture skin needles 181A and 181B each of which has an expanded portion 181c, by being operated in the forming step as follows.

2-3A: Forming Step/Needle Having Expanded Portion #1

Figure 21:
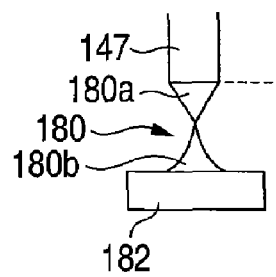
FIG. 21 is a view illustrating the behavior of a pin member in the process of forming the skin needle having the expanded portion and also illustrating an associated state of the material.
Figure 21:
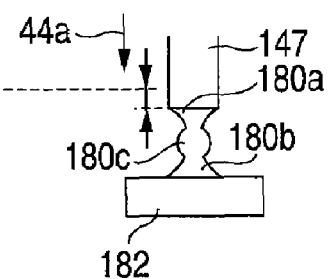
Figure 21:
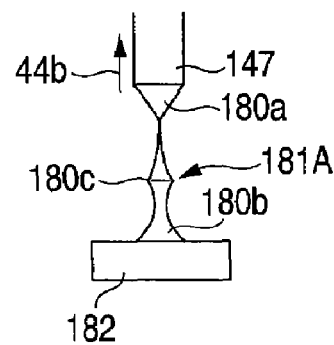
Figure 22:
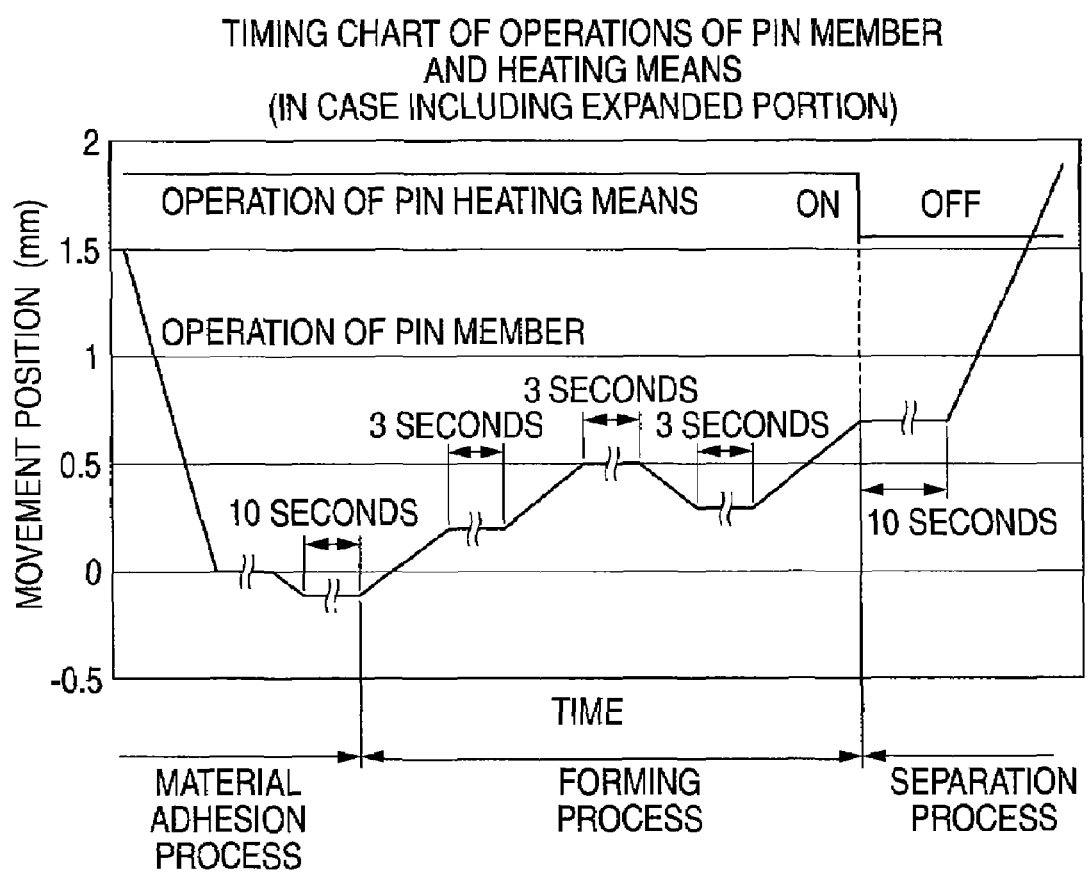
FIG. 22 is a view illustrating the behavior of a pin member in the process of forming the skin needle having the expanded portion and also illustrating an associated state of the material.

FIGS. 21(a) to 21(c) are views each illustrating the behavior of the pin member 147 in the process of forming the skin needle 181A having the expanded portion 181c and also illustrating an associated state of the material 180. Also, FIG. 22 is a view illustrating the behavior of the pin member 147 in the process of forming the skin needle having the expanded portion. In the forming step, the computer 50 operates the drive mechanism 48 to approach the pin member 147 to the base 182 by a predetermined amount, as illustrated in a timing chart shown in FIG. 22, halfway through drawing the base installation member 41 and the pin member 147 away from each other to draw out the material 180. According to this embodiment, the computer 50 operates the drive mechanism 48 to cause the pin member 147 to first the pin member 147 move upwardly by 300 μm. Then, the computer 50 stops an operation of the drive mechanism 48 about 3 seconds. Also, the computer 50 performs similar movement and stoppage to thereby gradually draw out the material 180 (see FIG. 21(a)). In this state, the material 180 is not sufficiently drawn out. Subsequently, the computer 50 operates the drive mechanism 48 (see FIG. 21(b)) to cause the pin members 147 to move downwardly by 200 μm. The downward movement of the pin members 147 is a movement contrary to the operation of drawing out the material 180. This movement compresses the material 180 having been drawn out, so that the material 180 is expanded in a direction (i.e., a radial direction) perpendicular to a drawing-out direction so as to form the expanded portion 180c. The pin members 147 stop at the position, to which the pin members 147 move down, by about 3 seconds. Subsequently, the pin members 147 rise again by 400 μm. Then, the material 180 starts being drawn out again. Even when the apparatus draws out the material, the expanded portion 180c changes the shape to reduce the size in a radial direction. Thus, the expanded portion 180c is left in a middle portion of the needle. The movement speed of each of the pin members 147 is about 2 mm/second. Thus, as illustrated in FIG. 21(c), the skin needle 181A having the expanded portion 180c is formed.

2-3B: Forming Step/Needle Having Expanded Portion #2

Figure 23:
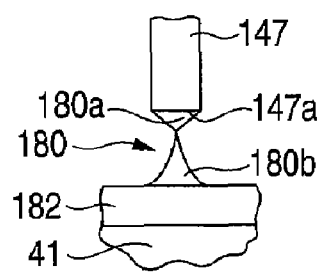
FIG. 23 is a view illustrating the behavior of a pin member in the process of forming the skin needle having the expanded portion and also illustrating an associated state of the material.
Figure 23:
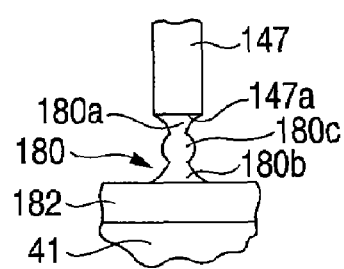
Figure 23:
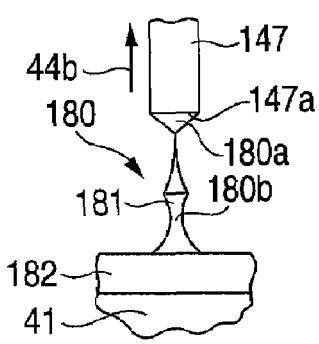

In addition to the above method, the following method described below is performed as another method of manufacturing a needle having the expanded portion 180c by the skin needle manufacturing apparatus 110 of the material drawing-up type. FIGS. 23(a) to 23(c) are views each illustrating the behavior of the pin member 147 in the process of forming the skin needle 181B having the expanded portion 181c according to this method and also illustrating an associated state of the material 180. In the forming step, the computer 50 stops an operation of the drive mechanism 48 to maintain the position of the pin member 147 (see FIG. 23(a)) halfway through drawing the base installation member 41 and the pin member 147 to draw out the material 180. In a case where the stoppage state is maintained for a time period equal to or longer than a predetermined value (e.g., 20 seconds), a part of the adhesion portion 180a of the material 180, which is positioned at an upper place, moves down due to an own weight thereof, so that the expanded portion 180c radially expanded is formed, as illustrated in FIG. 23(b). The downward movement of the adhesion portion 180a is a movement contrary to the operation of drawing out the material 180. This movement generates a slack in the material 180 having been drawn out. The material 180 is expanded in a direction (i.e., a radial direction) perpendicular to the drawing-out direction, so that the expanded portion 180c is formed. Subsequently, even when the drive mechanism 48 is further operated to draw out the material 180, the expanded portion 180c changes the shape thereof and remains present therein. Consequently, the skin needle 181 a having the expanded portion 180c can be formed.

Figure 24:
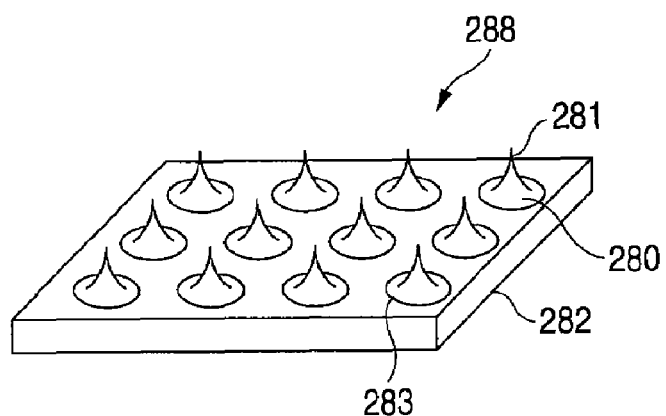
FIG. 24 is a partial appearance perspective view of a needle assembly including a plurality of skin needles manufactured by the skin needle manufacturing apparatus illustrated in FIG. 11.
Figure 25:
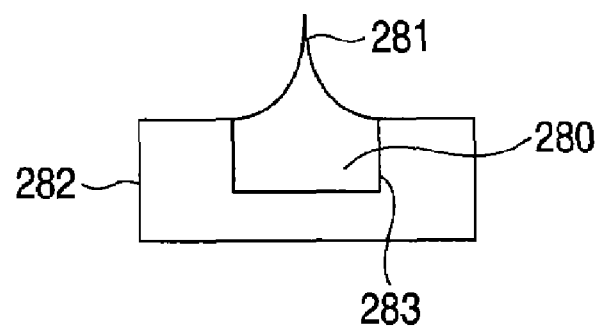
FIG. 25 is a cross-sectional view of a part of the needle assembly, which is shown in FIG. 14 and which is provided with the skin needle.

According to the present embodiment, in the skin needle manufacturing apparatus 110 of the material drawing-up type, the base 182, on which the skin needle 181 is erected, is formed of the material of the skin needle 181. At least a part of the base 182 is melted, so that the skin needle 181 is formed. However, a base 282 made of another material is used, instead of the base 182. The material of a needle is held by a part of the base 282, at which the skin needle is provided. The needle can be formed of the material held at the base 282. FIG. 24 is a view illustrating an example of the base 282 and illustrates an appearance perspective view of a needle assembly 288 obtained by erecting skin needles 281 on the base 282. FIG. 25 is a cross-sectional view of a part at, which the skin needle 281 is provided, in the needle assembly 288. The base 282 has a concave portion 283 for accumulating the material of the skin needle. A material 280 of the skin needle 281 is injected into the concave portion 283. Consequently, the material 280 of the skin noodle 281 can effectively be used by suppressing an amount of use of the material 280. Incidentally, the material 280 of the skin needle 281 is injected into the concave portion formed in the base 282 to enhance the adhesion of the material 280 to the base 282. However, the material 280 can be stuck to a surface of the base. In this case, the concave portion is unnecessary.

The skin needle manufacturing apparatus 110 of the material drawing-up type described above manufactures the skin needle 181 formed of the molten material 180 attached to the pin member 147. Thus, the mold as used according to the conventional technique is unnecessary. The skin needles 181 and 182 are integrated by drawing up the material from the base 182 to form the skin needle 181. Thus, the degree of attachment between the needle and the base can be enhanced. Thus, the apparatus is configured so that the skin needle 181 is not easily detached from the base 182. Also, the skin needles 182 of various shapes can be manufactured by changing the shape and the size of the end surface of each of the pin members 47 or changing the speed at which the pin member 147 and the base 182 are separated from each other.

Meanwhile, in the foregoing description, the skin needle manufacturing apparatus 10 of the material discharge type and that 110 of the material drawing-up type have been described. The skin needle manufacturing apparatuses 10 and 110 can manufacture the skin needles 81 and 181 arranged like grid-points. However, the skin needle manufacturing apparatuses 10 and 110 can manufacture a plurality of skin needles which are disposed in an arrangement other than the grid-point arrangement. Apparently, the skin needle manufacturing apparatuses 10 and 110 can manufacture a single skin needle.

Additionally, the skin needle manufacturing apparatuses 10 and 110 can implement the cooling of the separating portion of the materials 80 and 180 in the separation step of separating the materials of the skin needles 81 and 181 by natural heat radiation. However, the skin needle manufacturing apparatus 10 or 110 can have a cooling unit for positively cooling the material 80 or 180.

Manufacture of Two-Stage Skin Needle

Figure 26:
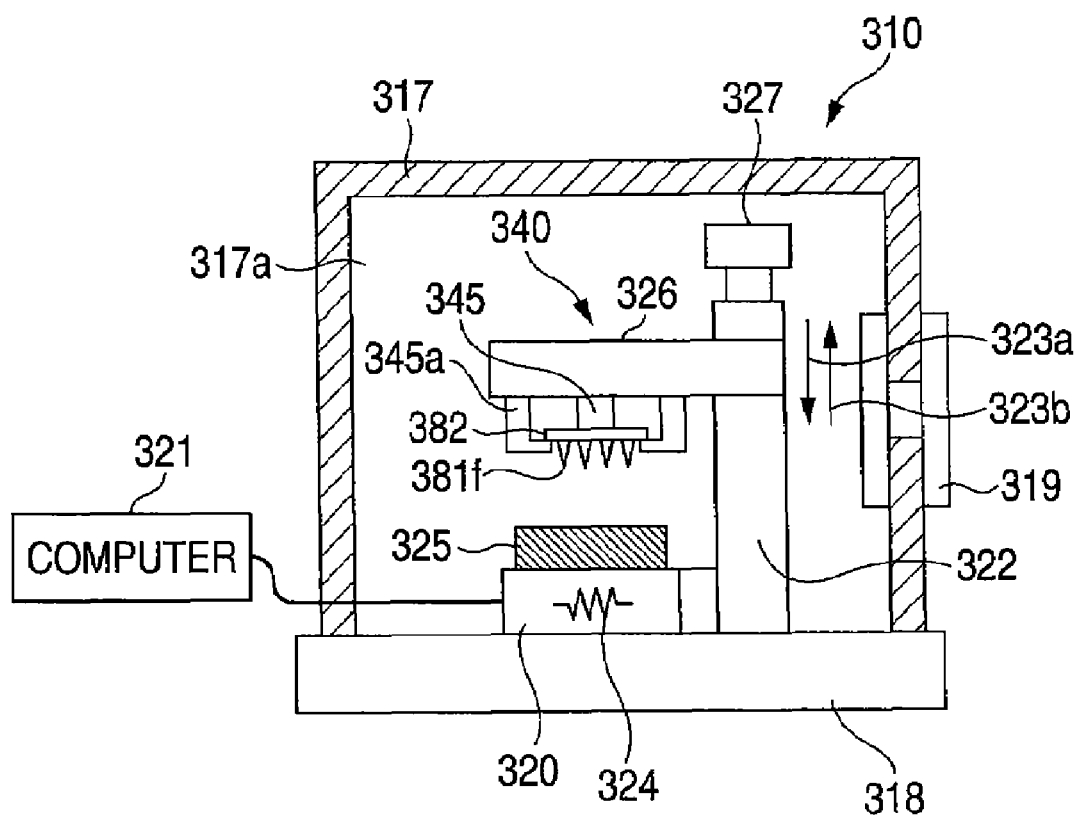
FIG. 26 is a view illustrating an embodiment of a second-stage skin needle manufacturing apparatus, which is a side cross-sectional view thereof.

Another skin needle made of a second material at a needle-point portion of the skin needle 81 or 181 is additionally formed at the needlepoint portion of the skin needle manufactured by the skin needle manufacture apparatus 10 or 110 which is the first or second embodiment. Thus, a two-stage skin needle having two stage needles provided in an axial direction can be manufactured. FIG. 26 is a view illustrating a skin needle manufacturing apparatus 310 for forming the two-stage skin needle 381. FIG. 27 is a partial appearance perspective view illustrating the needle assembly 388 including the two-stage skin needle 381. As illustrated in FIG. 27, the two-stage skin needle 381 employs the skin needle 81 or 181 manufactured by the skin needle manufacturing apparatus 10 or 110 as a first-stage needle 381f. A second-stage needle 381s is formed at the needlepoint portion of the first-stage needle 381f. This embodiment uses the material (i.e., a second material) of the second-stage needle 381s, which is formed of maltose that is a biodegradable substance as a major ingredient and which includes functional substances to be injected into skin. When the second-stage skin needle 381 is stabbed into the skin, the second-stage needle 381s placed at the end of the two-stage skin needle is fully inserted into an inner part of the skin, as compared with the first-stage needle 381f. Accordingly, the functional substances can effectively be injected into the inner part of the skin without waste.

As shown in FIG. 26, the two-stage skin needle manufacturing apparatus 310 has a wall portion 317 as an outer case. The wall portion 317 is installed onto a pedestal 318. A chamber 317a is formed in the wall portion 317. A humidity maintaining means 319 configured to maintain the inner humidity of the chamber 317a at 30% or less is installed in the wall portion 317. A body 340 of the two-stage skin needle manufacturing apparatus 310 is installed in the chamber 317a. The body 340 has a pillar portion 322 erected on the pedestal 318, a material installation member 325 disposed at the root of the pillar portion 322, a moving portion 322 supported upwardly and downwardly (i.e., in directions designated by arrows 323a and 323b in the drawings) movably along the pillar portion 322, and a drive mechanism 327 serving as a moving member for moving the moving portion 326. A second material 325 used as the material of the second-stage needle is installed on the top surface of the material installation member 320. The material installation member 320 is configured to be heated by the heat generating means 324 provided therein. A base holding member 345 holding a base 382, on which the first-stage needle 318f, is positioned above the material installation member 320. The base holding member 345, together with a base support 345a aiding the holding of the base 382 by supporting the base 382 from below, is fixed to the bottom surface of an end portion of the moving portion 326. An operation of each of the heat generating means 324 and the drive mechanism 327 is controlled by a computer 321 serving as the control means. The drive mechanism 327 moves the base holding member 345 fixed to the moving portion 326 in a direction, in which the base holding member 345 approaches and departs from the material installation member 320, by moving the moving portion 326 along the pillar portion 322.

An operation of the skin needle manufacturing apparatus 310 is described below. FIGS. 28(a) and 28(b) are views illustrating a movement of the first-stage needle 381f in the forming step of forming the second-stage needle 381a, and the associated forming state of the second-stage needle 381s, respectively.

3-1: Second-Material Melting Step

First, as a two-stage skin needle manufacturing preparation stage for the two-stage skin needle 381, the second material 325 to be used as the material of the second-stage needle 381 is installed on the top surface of the material installation member 320. When a signal instructing the manufacture of the skin needle is input to the computer 321, the computer 321 first operates the heat generating means 324 and heats the material installation member 320. A heating temperature, at which the material installation member 320 is heated by the heat generating means 324, at that time is set at about 100° C. The second material 325 installed on the top surface of the material installation member 320 is melted by heating the material installation member 320. Incidentally, the heating of the material installation member 320 by the heat generating means 324 is continuously performed in the subsequent step or later.

3-2: Second-Material Adhesion Step

Next, the computer 321 operates the drive mechanism 327 and moves the moving portion 326 downwardly (i.e., in a direction designated by arrow 323a) along the pillar portion 322. Then, the base holding member 345 fixed to the moving portion 326 approaches the material installation member 320 to bring an end of the first-stage needle 381f held by the base holding member 345 into contact with the molten second material 325 on the material installation member 320 (see FIG. 28(a)). In this state, the second material 325 adheres to an end of the first-stage needle 381f.

4-3: Second-Stage Needle Forming Step

Next, the computer 321 operates the drive mechanism 327 and moves the moving portion 326 upwardly (i.e., in a direction designated by arrow 323b) along the pillar portion 322. Then, the base holding member 345 fixed to the moving portion 326 moves in a direction, in which the base holding member 345 departs from the material installation member 320. The second material 325 adhering to the end portion of the first-stage needle 381f is drawn out, so that the second-stage needle 381s can be formed (see FIG. 6(c)). At that time, the second-stage needle 381s is formed as a substantially spindle-shaped projection having a length of about 300 μm. As illustrated in FIG. 27, a plurality of first-stage needles 381f is arranged like grid-points substantially at uniform intervals. Thus, a plurality of second-stage needles 381s is arranged like grid-points substantially at uniform intervals. Additionally, the manufacturing apparatus can alternately repeat the adhesion step and the forming step at least twice, so that a skin needle having three stage needles or more can be formed.

INDUSTRIAL APPLICABILITY

As described above, the skin needle manufacturing apparatus and the skin needle manufacturing method according to the invention have advantages that skin needles can relatively easily be manufactured without excessive time, effort, and cost, as compared with the conventional apparatus and the conventional method. The skin needle manufacturing apparatus and the skin needle manufacturing method according to the invention are effective in manufacturing skin needles whose lengths are equal to or less than several hundreds micrometers.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A skin needle manufacturing apparatus, comprising:
 a base installation member configured to install a base on which one or more skin needles are erected;
 a pin member to which a part of a material of said skin needle adheres; and
 a moving unit configured to move at least one of said base installation member and said pin member in a direction in which said base installation member and said pin member relatively move away from each other,
 wherein said base installation member and said pin member are separated by said moving unit from each other in a state in which said material is melted and adheres to said pin member and to said base, so as to draw out said molten material to form a skin needle.

2. The skin needle manufacturing apparatus according to claim 1, wherein said drawn-out material includes an adhesion portion which adheres to said pin member, and a projection portion which is erected on said base and is projected by a tensile force generated between said base and said adhesion portion, and wherein said projection portion erected on said base is formed as said skin needle.

3. The skin needle manufacturing apparatus according to claim 2, further comprising a heat generator configured to adjust said material to a predetermined temperature.

4. The skin needle manufacturing apparatus according to claim 3, wherein said heat generator includes a base heater configured to heat said base installation member and to adjust said projection portion of said material to a predetermined temperature.

5. The skin needle manufacturing apparatus according to claim 3, wherein said heat generator includes a pin heater configured to heat said pin member and to adjust said adhesion portion of said material, which has adhered to said pin member, to a predetermined temperature.

6. The skin needle manufacturing apparatus according to claim 3, wherein said heat generator includes a base heater configured to heat said base installation member and to adjust said projection portion of said material to a predetermined temperature, and also includes a pin heater configured to heat said pin member and to adjust said adhesion portion of said material, which has adhered to said pin member, to a predetermined temperature.

7. The skin needle manufacturing apparatus according to claim 3, wherein said pin member is a hollow pin having a fine hole provided therein and discharges said material to said base.

8. The skin needle manufacturing apparatus according to claim 7, further comprising:
 a container configured to accommodated said molten material; and
 a pressure controller configured to control a pressure applied to said material accommodated in said container to discharge said material from said fine hole.

9. The skin needle manufacturing apparatus according to claim 8, further comprising:

said heater includes a container heater configured to heat said container and to adjust said material in said container to a predetermined temperature.

10. The skin needle manufacturing apparatus according to claim 8, further comprising:
a controller configured to control said moving unit, said pressure controller, and said heat generator,
wherein said moving unit, said pressure controller, and said heat generator are operated by said controller to form said skin needle.

11. The skin needle manufacturing apparatus according to claim 7, wherein said material of said skin needle is formed mainly of biodegradable substances, and
wherein said base is configured so that a surface, on which said skin needle is erected, has hydrophilicity or adhesion.

12. The skin needle manufacturing apparatus according to claim 3, wherein said base is formed of said material of said skin needle, and wherein said skin needle is formed by melting at least a part of said base.

13. The skin needle manufacturing apparatus according to claim 3, wherein said material is held at a part of said base, at which said skin needle is provided, and wherein said skin needle is formed of said material held at said base.

14. The skin needle manufacturing apparatus according to claim 12, wherein a shape of an end surface of said pin member, with which said material is in contact, is substantially a sphere, a circle, or a regular polygon.

15. The skin needle manufacturing apparatus according to claim 12, wherein a shape of an end surface of said pin member, with which said material is in contact, is substantially a rectangle.

16. The skin needle manufacturing apparatus according to claims 3, further comprising:
a controller configured to control said moving unit, and said heat generator,
wherein said moving unit, and said heat generator are operated by said controller to form said skin needle.

17. The skin needle manufacturing apparatus according to claim 16, wherein said controller controls, before said material is drawn out, said moving unit in a state, in which said pin member and said base are in contact with said material, to cause said base installation member and said pin member to approach each other by a predetermined amount.

18. The skin needle manufacturing apparatus according to claim 16, wherein said controller alternately repeats, when said material is drawn out, an operation and a stoppage of said moving unit in stages.

19. The skin needle manufacturing apparatus according to claim 16, wherein after said molten material is drawn out by said moving unit and said heat generator, said controller stops an operation of said moving unit for a predetermined time and subsequently cuts off said adhesion portion from said projection portion by further drawing said base installation member and said pin member away from each other.

20. The skin needle manufacturing apparatus according to claim 19, wherein when said controller stops an operation of said moving unit for a predetermined time after said material is drawn out, said controller stops an operation of said heat generator or lower the preset temperature.

21. The skin needle manufacturing apparatus according to claim 10, wherein in a case where said pin member is said hollow pin, said controller operates said moving unit to further discharge said material from said fine hole of said hollow pin halfway through further drawing said base installation member and said pin member away from each other by operating the moving unit to draw out said material.

22. The skin needle manufacturing apparatus according to claim 16, wherein when said pin member is said hollow pin, said controller operates said moving unit and causes said base installation member and said pin member to once approach each other halfway through further drawing said base installation member and said pin member away from each other by operating the moving unit to draw out said material.

23. The skin needle manufacturing apparatus according to claim 16, wherein when said pin member is said hollow pin, said controller temporarily stops an operation of said moving unit and maintains a stopped state so that a part of said adhesion portion or said projection portion of said material moves in a direction opposite to a direction, in which said material is drawn out, due to an own weight thereof, halfway through further drawing said base installation member and said pin member away from each other to draw out said material.

24. The skin needle manufacturing apparatus according to claim 1, further comprising a humidity maintaining unit configured to maintain humidity around said material at a predetermined value or less.

25. A two-stage skin needle manufacturing apparatus configured to manufacture a two-stage skin needle in an axial direction by employing said skin needle formed in said skin needle manufacturing apparatus according to claim 1 as a first-stage needle, and by forming a second-stage skin needle made of a second material at a needlepoint portion of said first-stage needle, said two-stage skin needle manufacturing apparatus, comprising:
a base holding member configured to hold a base, on which said first-stage needle is erected;
a material installation member at which said second material is installed; and
a second moving unit configured to move at least one of said base holding member and said material installation member in a direction in which said base holding member and said material installation member relatively move away from each other, and
wherein said second moving unit draws said base holding member and said material installation member away from each other, in a state in which said second material is melted and adheres to said needlepoint portion, so as to form said second-stage skin needle.

26. The two-stage skin needle manufacturing apparatus according to claim 25, further comprising:
a second heat generator configured to adjust said second material to a predetermined temperature by heating said material installation member; and
a second controller configured to control said second heat generator and said second moving unit, and
wherein said second control unit operates said second heat generating unit and said second moving unit to form said second-stage skin needle.

27. A manufacturing method for a skin needle, wherein a material of said skin needle, which is in a molten state, is provided on a base, on which one or more skin needles are erected, that a pin member is attached to a part of said molten material, and that said base and said pin member are drawn away from each other in a direction in which said base and said pin member relatively move away from each other, thereby to form a skin needle.

28. The skin needle manufacturing method according to claim 27, wherein said drawn-out material includes an adhesion portion which adheres to said pin member, and a projection portion which is erected on said base and is projected by a tensile force generated between said base and said adhesion portion, and wherein said projection portion erected on said base is formed as said skin needle.

29. The skin needle manufacturing method according to claim 28, wherein when said material is drawn out, said material is adjusted to a predetermined temperature by a heat generator.

30. The skin needle manufacturing method according to claim 29, wherein said heat generator adjusts a temperature of at least one of said adhesion portion and said projection portion of said material.

31. The skin needle manufacturing method according to claim 29, wherein said material of said skin needle in a state, in which said pin member is melted to an end thereof, is discharged to said base.

32. The skin needle manufacturing method according to claim 29, wherein said base is formed of said material of said skin needle, and wherein said skin needle is formed by melting at least a part of said base.

33. The skin needle manufacturing method according to claim 29, wherein said material is held at a part of said base, at which said skin needle is provided, and wherein said skin needle is formed of said material held at said base.

34. The skin needle manufacturing method according to claim 29, wherein before said material is drawn out, said base installation member and said pin member are caused to approach each other by a predetermined amount in a state, in which at least said pin member and said base are in contact with said material, to cause.

35. The skin needle manufacturing method according to claim 29, wherein when said material is drawn out, said base and said member are drawn away from each other in stages.

36. The skin needle manufacturing method according to claim 29, wherein after said molten material is drawn out, a distance between said base and said pin member is maintained for a predetermined time, and subsequently, said adhesion portion is cut off from said projection portion by further drawing said base installation member and said pin member away from each other.

37. The skin needle manufacturing method according to claim 36, wherein when said distance between said base and said pin member is maintained for the predetermined time after said material is drawn out, an operation of said heat generator is stopped, alternatively, the preset temperature is lowered.

38. The skin needle manufacturing method according to claim 31, wherein when said material is drawn out, said material melted from an end of said pin member is further discharged halfway through drawing said base installation member and said pin member away from each other.

39. The skin needle manufacturing method according to claim 29, wherein when said material is drawn out, said base and said pin member are caused to once approach each other halfway through drawing said base and said pin member away from each other.

40. The skin needle manufacturing method according to claim 29, wherein when said material is drawn out, halfway through drawing said base and said pin member away from each other to draw out said material, an operation of drawing said base and said pin member away from each other is temporarily stopped, and a stopped state is maintained so that a part of said adhesion portion or said projection portion of said material moves in a direction opposite to a direction, in which said material is drawn out, due to an own weight thereof.

41. A two-stage-skin-needle manufacturing method for manufacturing a two-stage skin needle having two-stage needles provided in an axial direction by employing said skin needle formed in said skin needle manufacturing apparatus according to claim 27 as a first-stage needle, and by forming a second-stage skin needle made of a second material at a needlepoint portion of said first-stage needle, said two-stage-skin-needle manufacturing method, wherein said second material put in a state, in which at least a part thereof is melted, is installed in a material installation member;

said molten second material is caused to adhere to a needlepoint portion of said first-stage needle; and said second material is drawn out by drawing said base holding member and said material installation member away from each other in a direction in which said base holding member and said material installation member relatively move away from each other, so as to form said second-stage skin needle.

42. The two-stage-skin-needle manufacturing method according to claim 41, wherein each of a material of said first-stage needle and said second material is formed mainly of biodegradable substances, and wherein said second material includes functional substances.

\* \* \* \* \*